(12) United States Patent
Pajouhesh et al.

(10) Patent No.: US 7,244,758 B2
(45) Date of Patent: Jul. 17, 2007

(54) N-TYPE CALCIUM CHANNEL BLOCKERS

(75) Inventors: Hassan Pajouhesh, Vancouver (CA); Terrance P. Snutch, Vancouver (CA); Hossein Pajouhesh, Burnaby (CA); Yanbing Ding, Vancouver (CA)

(73) Assignee: Neuromed Pharmaceuticals Ltd., Vancouver BC (CA)

( * ) Notice: Subject to any disclaimer, the term of this patent is extended or adjusted under 35 U.S.C. 154(b) by 346 days.

(21) Appl. No.: 10/856,921

(22) Filed: May 28, 2004

(65) Prior Publication Data

US 2005/0014748 A1 Jan. 20, 2005

Related U.S. Application Data

(60) Provisional application No. 60/474,864, filed on May 30, 2003.

(51) Int. Cl.
*A61K 31/40* (2006.01)
*C07D 207/00* (2006.01)

(52) U.S. Cl. .............. 514/408; 514/423; 548/530; 548/539

(58) Field of Classification Search .......... 548/530, 548/539; 514/408, 423
See application file for complete search history.

(56) References Cited

U.S. PATENT DOCUMENTS

| | | | | |
|---|---|---|---|---|
| 5,116,851 | A | * 5/1992 | Krapcho et al. | .......... 514/354 |
| 5,386,025 | A | 1/1995 | Jay et al. | ............ 536/23.5 |
| 5,395,832 | A | * 3/1995 | Ito et al. | .......... 514/210.16 |
| 5,428,038 | A | 6/1995 | Chatterjee et al. | ........ 514/252.2 |
| 5,623,051 | A | 4/1997 | Catterall et al. | ............ 530/324 |
| 5,646,149 | A | 7/1997 | Hellberg et al. | ........ 514/254.11 |
| 5,703,071 | A | 12/1997 | Itoh et al. | ............ 514/218 |
| 6,011,035 | A | 1/2000 | Snutch et al. | .......... 514/255.01 |
| 6,166,037 | A | * 12/2000 | Budhu et al. | ............ 514/326 |
| 6,294,533 | B1 | 9/2001 | Snutch et al. | ............ 514/231.2 |
| 6,310,059 | B1 | 10/2001 | Snutch | .......... 514/222.2 |
| 6,387,897 | B1 | 5/2002 | Snutch | .......... 514/231.2 |

FOREIGN PATENT DOCUMENTS

| | | |
|---|---|---|
| EP | 0 640 601 | 3/1995 |
| WO | WO 92/22527 | 12/1992 |
| WO | WO 97/27180 | 7/1997 |
| WO | WO 99/09984 | 3/1999 |
| WO | WO 03/029199 | 4/2003 |

OTHER PUBLICATIONS

Ito et al. 1993, CAS: 118:80825.*
Cox and Denyer, Expert Opinion on Therapeutic Patents (1998) 8(10):1237-1250.
International Search Report for PCT/CA2004/000797, mailed on Aug. 30, 2004, 7 pages.
Valenta et al., Collection of Czechoslovak Chemical Communications (1994) 59(5):1126-1136.
Bourinet et al., Nature Neuroscience (1999) 2:407-415.
Cribbs et al., Circulation Research (1998) 83:103-109.
Dooley, Current Opinion in CPNS Investigational Drugs (1999) 1:116-125.
Dunlap et al., Trends Neurosci (1995) 18:89-98.
Gould et al., Proc. Natl. Acad. Sci. USA (1983) 80:5122-5125.
Grantham et al., Brit. J. Pharmacol. (1944) 111:483-488.
King et al., J. Biol. Chem. (1989) 264:5633-5641.
Lee et al., Journal of Neuroscience (1999) 19:1912-1921.
McCleskey et al., Curr. Topics. Membr. (1991) 39:295-326.
Perez-Reyes et al., Nature (1998) 391:896-900.
Sather et al., Nueron (1993) 11:291-303.
Stea et al., Proc. Natl. Acad. Sci. USA (1994) 91:10576-10580.

* cited by examiner

*Primary Examiner*—Kamal A. Saeed
*Assistant Examiner*—Rei-tsang Shiao
(74) *Attorney, Agent, or Firm*—Morrison & Foerster LLP

(57) ABSTRACT

Compounds that are derivatives of 3-aminomethyl-pyrrolidine generally containing at least one benzhydril moiety are useful in treating conditions which benefit from blocking calcium ion channels.

18 Claims, 14 Drawing Sheets

| # | Name | Structure |
|---|---|---|
| P1 | N-(1-Benzhydryl-pyrrolidin-3-ylmethyl)-3,3-diphenyl-propionamide | 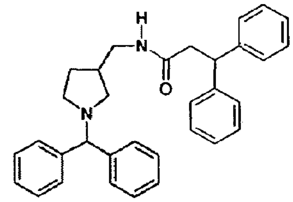 |
| P2 | 1-{3-[(Benzhydryl-amino)-methyl]-pyrrolidin-1-yl}-3,3-diphenyl-propan-1-one | 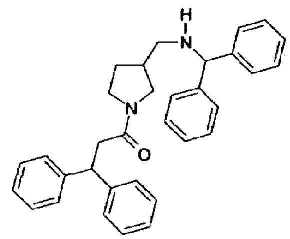 |
| P3 | N-{1-[6,6-Bis-(4-fluoro-phenyl)-hexanoyl]-pyrrolidin-3-ylmethyl}-3,4,5-trimethoxy-benzamide | 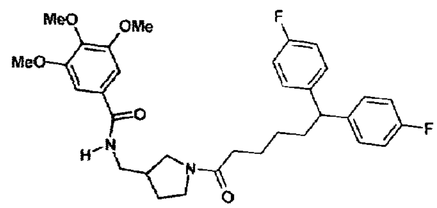 |
| P4 | {1-[6,6-Bis-(4-fluoro-phenyl)-hexyl]-pyrrolidin-3-ylmethyl}-(3,4,5-trimethoxy-benzyl)-amine | 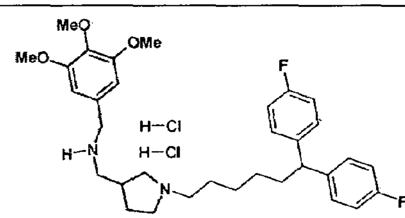 |
| P5 | 6,6-Bis-(4-fluoro-phenyl)-hexanoic acid [1-(3,4,5-trimethoxy-benzoyl)-pyrrolidin-3-ylmethyl]-amide | 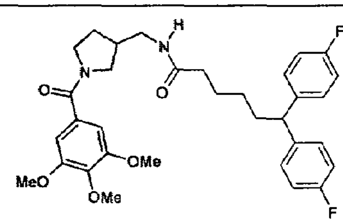 |
| P6 | [6,6-Bis-(4-fluoro-phenyl)-hexyl]-[1-(3,4,5-trimethoxy-benzyl)-pyrrolidin-3-ylmethyl]-amine | 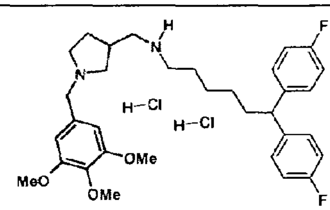 |

Figure 1

| # | Name | Structure |
|---|---|---|
| P7 | N-{1-[6,6-Bis-(4-fluoro-phenyl)-hexanoyl]-pyrrolidin-3-ylmethyl}-3,5-di-tert-butyl-4-hydroxy-benzamide | 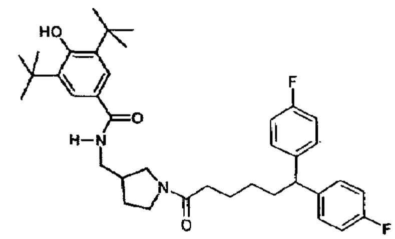 |
| P8 | 4-[({1-[6,6-Bis-(4-fluoro-phenyl)-hexyl]-pyrrolidin-3-ylmethyl}-amino)-methyl]-2,6-di-tert-butyl-phenol | 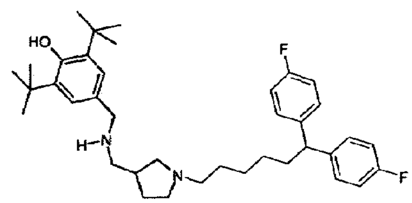 |
| P9 | 6,6-Bis-(4-fluoro-phenyl)-hexanoic acid [1-(3,5-di-tert-butyl-4-hydroxy-benzoyl)-pyrrolidin-3-ylmethyl]-amide | 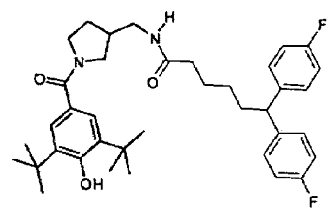 |
| P10 | 4-(3-{[6,6-Bis-(4-fluoro-phenyl)-hexylamino]-methyl}-pyrrolidin-1-ylmethyl)-2,6-di-tert-butyl-phenol | 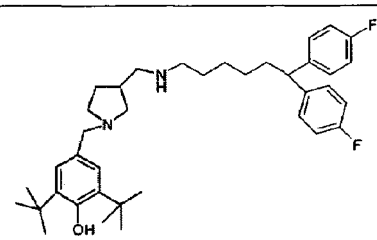 |
| P11 | 6,6-Bis-(4-fluoro-phenyl)-hexanoic acid [1-(3,5-di-tert-butyl-4-methoxy-benzoyl)-pyrrolidin-3-ylmethyl]-amide | 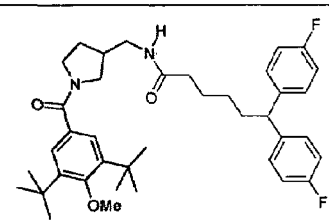 |

Figure 1

| # | Name | Structure |
|---|---|---|
| P12 | [6,6-Bis-(4-fluoro-phenyl)-hexyl]-[1-(3,5-di-tert-butyl-4-methoxy-benzyl)-pyrrolidin-3-ylmethyl]-amine | 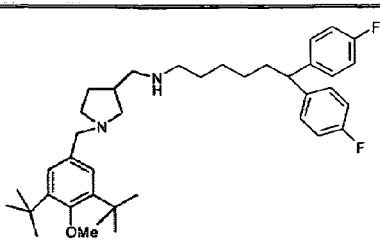 |
| P13 | N-{1-[6,6-Bis-(4-fluoro-phenyl)-hexanoyl]-pyrrolidin-3-ylmethyl}-3,5-di-tert-butyl-4-methoxy-benzamide | 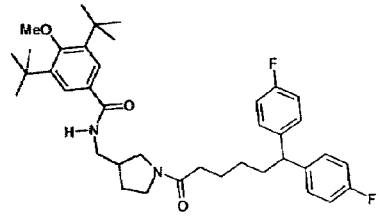 |
| P14 | {1-[6,6-Bis-(4-fluoro-phenyl)-hexyl]-pyrrolidin-3-ylmethyl}-(3,5-di-tert-butyl-4-methoxy-benzyl)-amine | 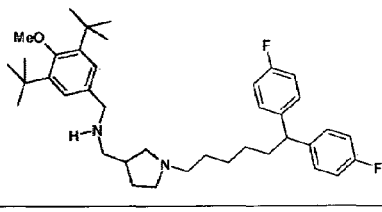 |
| P15 | N-{1-[6,6-Bis-(4-fluoro-phenyl)-hexanoyl]-pyrrolidin-3-ylmethyl}-3,5-dibromo-4-hydroxy-benzamide | 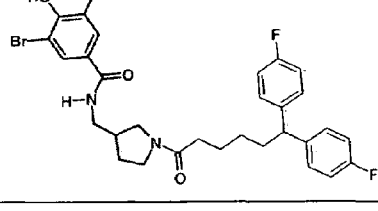 |
| P16 | 4-[({1-[6,6-Bis-(4-fluoro-phenyl)-hexyl]-pyrrolidin-3-ylmethyl}-amino)-methyl]-2,6-dibromo-phenol | 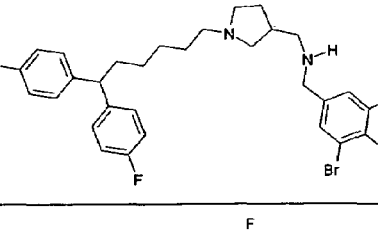 |
| P17 | N-{1-[6,6-Bis-(4-fluoro-phenyl)-hexanoyl]-pyrrolidin-3-ylmethyl}-3,5-di-tert-butyl-benzamide | 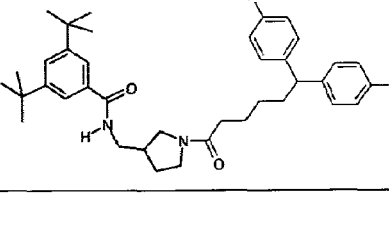 |

Figure 1

| # | Name | Structure |
|---|---|---|
| P18 | {1-[6,6-Bis-(4-fluoro-phenyl)-hexyl]-pyrrolidin-3-ylmethyl}-(3,5-di-tert-butyl-benzyl)-amine | 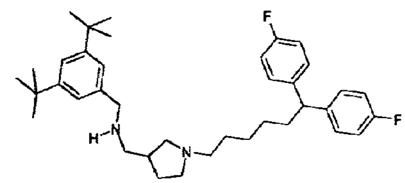 |
| P19 | N-{1-[6,6-Bis-(4-fluoro-phenyl)-hexyl]-pyrrolidin-3-ylmethyl}-3,5-di-tert-butyl-4-methoxy-benzamide | 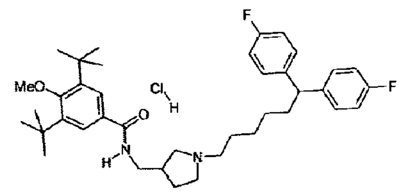 |
| P20 | N-{1-[6,6-Bis-(4-fluoro-phenyl)-hexyl]-pyrrolidin-3-ylmethyl}-3,4,5-trimethoxy-benzamide | 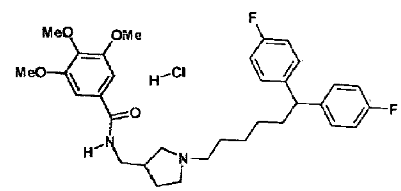 |
| P21 | N-{1-[6,6-Bis-(4-fluoro-phenyl)-hexyl]-pyrrolidin-3-ylmethyl}-3,5-bis-trifluoromethyl-benzamide | 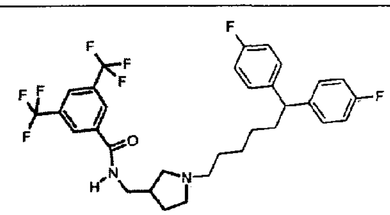 |
| P22 | N-{1-[6,6-Bis-(4-fluoro-phenyl)-hexanoyl]-pyrrolidin-3-ylmethyl}-3,5-di-tert-butyl-4-(2-dimethylamino-ethoxy)-benzamide | 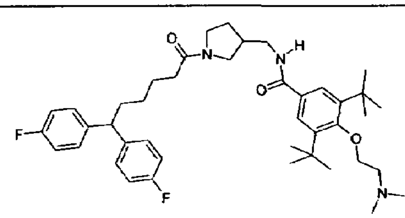 |
| P23 | 6,6-Bis-(4-fluoro-phenyl)-hexanoic acid {1-[3,5-di-tert-butyl-4-(2-dimethylamino-ethoxy)-benzoyl]-pyrrolidin-3-ylmethyl}-amide | 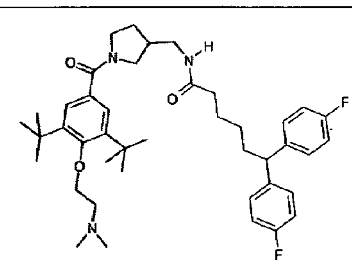 |

Figure 1

| # | Name | Structure |
|---|---|---|
| P24 | N-{1-[6,6-Bis-(4-fluoro-phenyl)-hexanoyl]-pyrrolidin-3-ylmethyl}-3,5-bis-trifluoromethyl-benzamide | 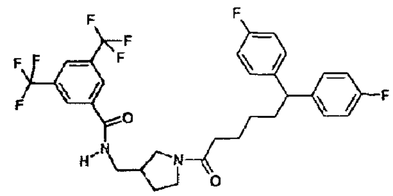 |
| P25 | N-{1-[6,6-Bis-(4-fluoro-phenyl)-hexanoyl]-pyrrolidin-3-ylmethyl}-4-tert-butyl-benzamide | 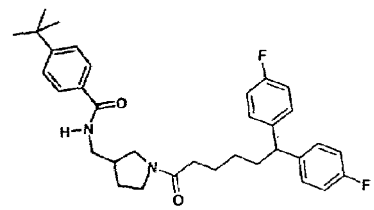 |
| P26 | N-{1-[(4-Chloro-phenyl)-phenyl-methyl]-pyrrolidin-3-ylmethyl}-3,3-diphenyl-propionamide | 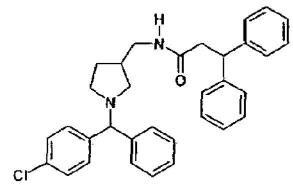 |
| P27 | N-{1-[6,6-Bis-(4-fluoro-phenyl)-hexanoyl]-pyrrolidin-3-ylmethyl}-2-phenoxy-acetamide | 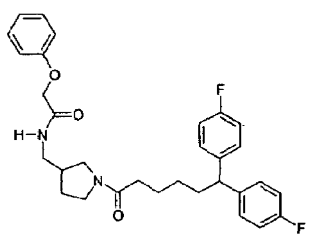 |
| P28 | N-{1-[6,6-Bis-(4-fluoro-phenyl)-hexanoyl]-pyrrolidin-3-ylmethyl}-2-phenylsulfanyl-acetamide | 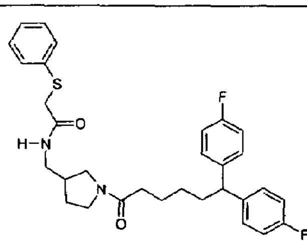 |

Figure 1

| # | Name | Structure |
|---|---|---|
| P29 | N-{1-[6,6-Bis-(4-fluoro-phenyl)-hexanoyl]-pyrrolidin-3-ylmethyl}-2-phenylamino-acetamide | 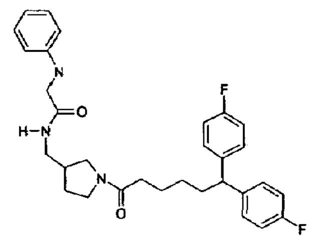 |
| P30 | N-[2-({1-[6,6-Bis-(4-fluoro-phenyl)-hexanoyl]-pyrrolidin-3-ylmethyl}-amino)-ethyl]-3,4,5-trimethoxy-benzamide | 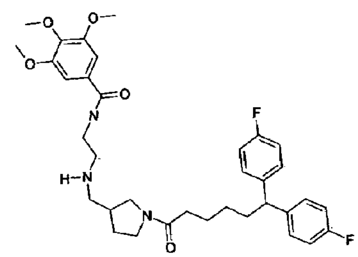 |
| P31 | N-{1-[6,6-Bis-(4-fluoro-phenyl)-hexanoyl]-pyrrolidin-3-ylmethyl}-2-(2,4-difluoro-phenoxy)-acetamide | 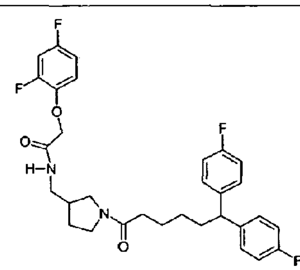 |
| P32 | 1-(1-Benzhydryl-pyrrolidin-3-ylmethyl)-1-(3,3-diphenyl-propionyl)-3-ethyl-urea | 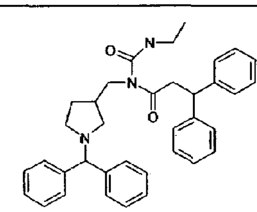 |
| P33 | 1-{1-[6,6-Bis-(4-fluoro-phenyl)-hexanoyl]-pyrrolidin-3-ylmethyl}-3-ethyl-1-(2-phenylsulfanyl-acetyl)-urea | 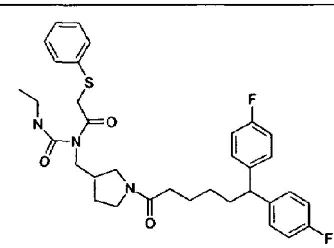 |

Figure 1

| # | Name | Structure |
|---|---|---|
| P34 | 1-{1-[6,6-Bis-(4-fluoro-phenyl)-hexanoyl]-pyrrolidin-3-ylmethyl}-3-ethyl-1-(2-phenylamino-acetyl)-urea | 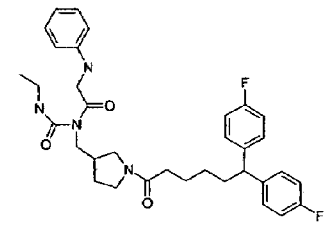 |
| P35 | 1-{1-[6,6-Bis-(4-fluoro-phenyl)-hexanoyl]-pyrrolidin-3-ylmethyl}-1-[2-(2,4-difluoro-phenoxy)-acetyl]-3-ethyl-urea | 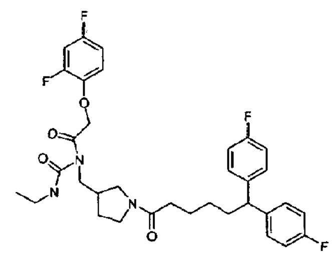 |
| P36 | N-{1-[6,6-Bis-(4-fluoro-phenyl)-hexanoyl]-pyrrolidin-3-ylmethyl}-2-(4-chloro-phenoxy)-acetamide | 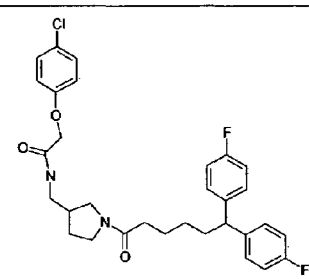 |
| P37 | N-{1-[(2-Chloro-phenyl)-phenyl-methyl]-pyrrolidin-3-ylmethyl}-3,3-diphenyl-propionamide | 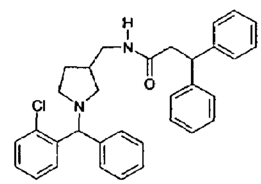 |
| P38 | N-{1-[(3-Chloro-phenyl)-phenyl-methyl]-pyrrolidin-3-ylmethyl}-3,3-diphenyl-propionamide | 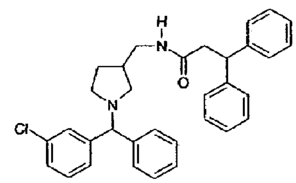 |

Figure 1

| # | Name | Structure |
|---|------|-----------|
| P39 | 3,3-Diphenyl-N-{1-[phenyl-(4-trifluoromethyl-phenyl)-methyl]-pyrrolidin-3-ylmethyl}-propionamide | 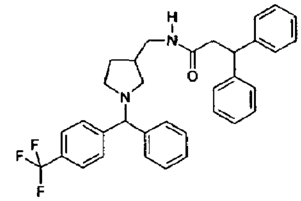 |
| P40 | N-{1-[6,6-Bis-(4-fluoro-phenyl)-hexanoyl]-pyrrolidin-3-ylmethyl}-2-(3,5-dimethyl-phenylamino)-acetamide | 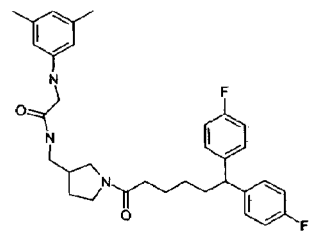 |
| P41 | N-{1-[6,6-Bis-(4-fluoro-phenyl)-hexanoyl]-pyrrolidin-3-ylmethyl}-2-(3,5-dimethyl-phenylamino)-acetamide | 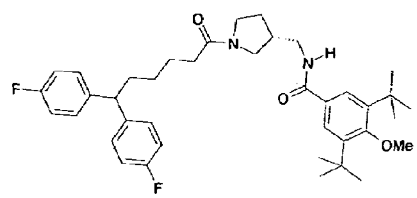 |
| P42 | R-N-{1-[6,6-Bis-(4-fluoro-phenyl)-hexanoyl]-pyrrolidin-3-ylmethyl}-3,5-di-tert-butyl-4-methoxy-benzamide | 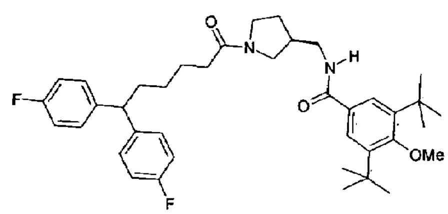 |
| P43 | S-N-{1-[6,6-Bis-(4-fluoro-phenyl)-hexanoyl]-pyrrolidin-3-ylmethyl}-3,5-di-tert-butyl-4-methoxy-benzamide | 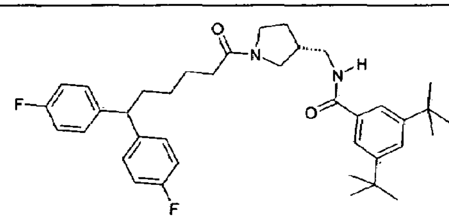 |
| P44 | R-N-{1-[6,6-Bis-(4-fluoro-phenyl)-hexanoyl]-pyrrolidin-3-ylmethyl}-3,5-di-tert-butyl-benzamide | 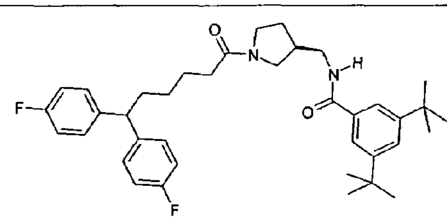 |

Figure 1

| # | Name | Structure |
|---|---|---|
| P45 | S-N-{1-[6,6-Bis-(4-fluoro-phenyl)-hexanoyl]-pyrrolidin-3-ylmethyl}-3,5-di-tert-butyl-benzamide | 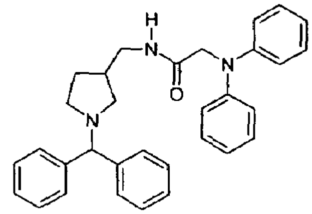 |
| P46 | N-(1-Benzhydryl-pyrrolidin-3-ylmethyl)-2-diphenylamino-acetamide | 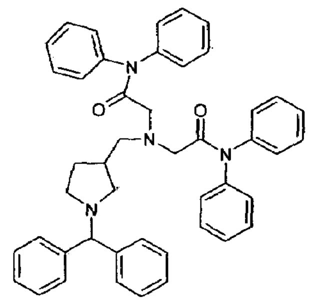 |
| P47 | 2-{(1-Benzhydryl-pyrrolidin-3-ylmethyl)-[(diphenylcarbamoyl)-methyl]-amino}-N,N-diphenyl-acetamide | 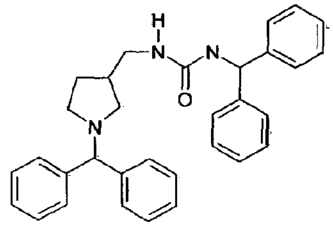 |
| P48 | 1-Benzhydryl-3-(1-benzhydryl-pyrrolidin-3-ylmethyl)-urea | 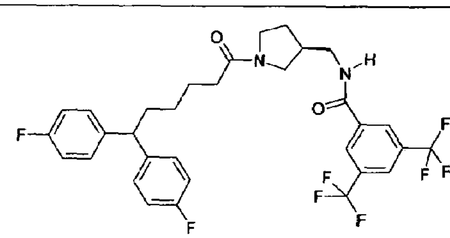 |
| P49 | S-N-{1-[6,6-Bis-(4-fluoro-phenyl)-hexanoyl]-pyrrolidin-3-ylmethyl}-3,5-bis-trifluoromethyl-benzamide | 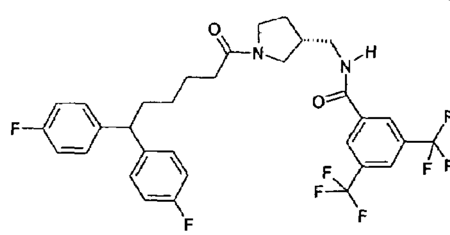 |

Figure 1

| # | Name | Structure |
|---|---|---|
| P50 | R-N-{1-[6,6-Bis-(4-fluoro-phenyl)-hexanoyl]-pyrrolidin-3-ylmethyl}-3,5-bis-trifluoromethyl-benzamide | 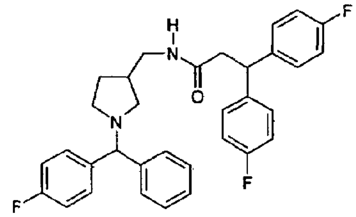 |
| P51 | 3,3-Bis-(4-fluoro-phenyl)-N-{1-[(4-fluoro-phenyl)-phenyl-methyl]-pyrrolidin-3-ylmethyl}-propionamide | 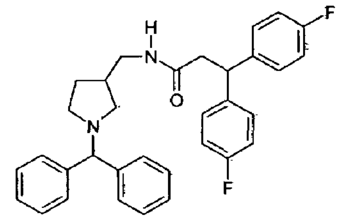 |
| P52 | N-(1-Benzhydryl-pyrrolidin-3-ylmethyl)-3,3-bis-(4-fluoro-phenyl)-propionamide | 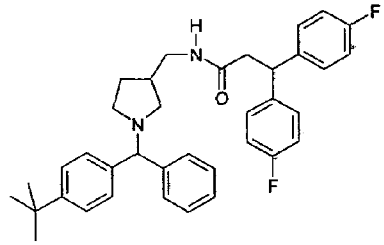 |
| P53 | N-{1-[(4-tert-Butyl-phenyl)-phenyl-methyl]-pyrrolidin-3-ylmethyl}-3,3-bis-(4-fluoro-phenyl)-propionamide | 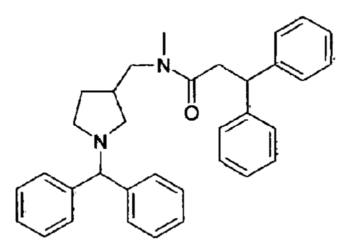 |
| P54 | N-(1-Benzhydryl-pyrrolidin-3-ylmethyl)-N-methyl-3,3-diphenyl-propionamide | 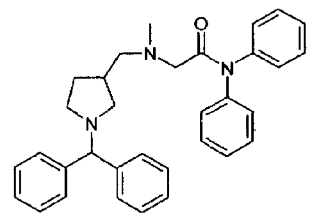 |

Figure 1

| # | Name | Structure |
|---|---|---|
| P55 | 2-[(1-Benzhydryl-pyrrolidin-3-ylmethyl)-methyl-amino]-N,N-diphenyl-acetamide | 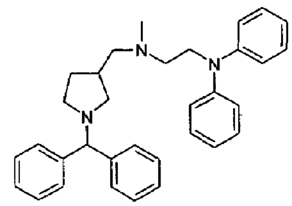 |
| P56 | N-(1-Benzhydryl-pyrrolidin-3-ylmethyl)-N-methyl-N',N'-diphenyl-ethane-1,2-diamine | 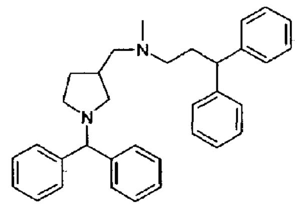 |
| P57 | (1-Benzhydryl-pyrrolidin-3-ylmethyl)-(3,3-diphenyl-propyl)-methyl-amine | 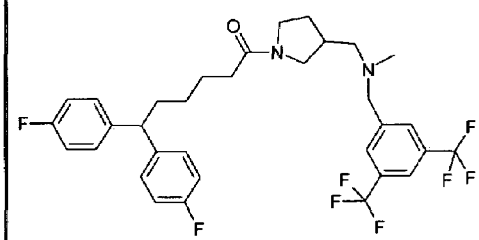 |
| P58 | 1-(3-{[(3,5-Bis-trifluoromethyl-benzyl)-methyl-amino]-methyl}-pyrrolidin-1-yl)-6,6-bis-(4-fluoro-phenyl)-hexan-1-one | 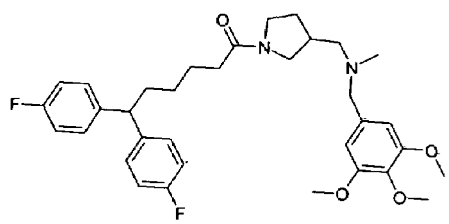 |
| P59 | 6,6-Bis-(4-fluoro-phenyl)-1-(3-{[methyl-(3,4,5-trimethoxy-benzyl)-amino]-methyl}-pyrrolidin-1-yl)-hexan-1-one | 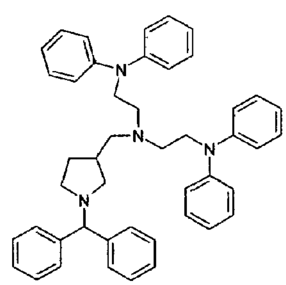 |

Figure 1

| # | Name | Structure |
|---|---|---|
| P60 | N-(1-Benzhydryl-pyrrolidin-3-ylmethyl)-N-(2-diphenylamino-ethyl)-N',N'-diphenyl-ethane-1,2-diamine | 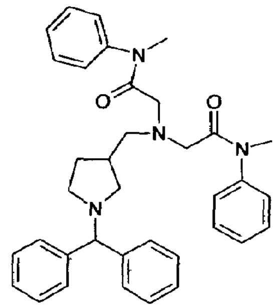 |
| P61 | N-{1-[6,6-Bis-(4-fluoro-phenyl)-hexanoyl]-pyrrolidin-3-ylmethyl}-3-fluoro-5-trifluoromethyl-benzamide | 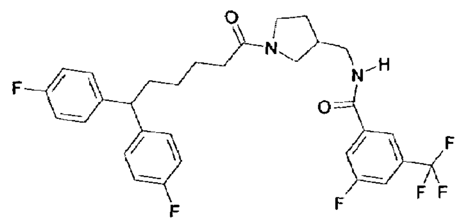 |
| P62 | N-{1-[6,6-Bis-(4-fluoro-phenyl)-hexanoyl]-pyrrolidin-3-ylmethyl}-4-fluoro-3-trifluoromethyl-benzamide | 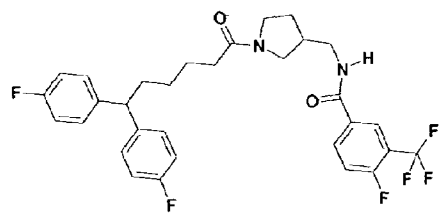 |
| P63 | [3-({[6,6-Bis-(4-fluoro-phenyl)-hexyl]-methyl-amino}-methyl)-pyrrolidin-1-yl]-(3,4,5-trimethoxy-phenyl)-methanone | 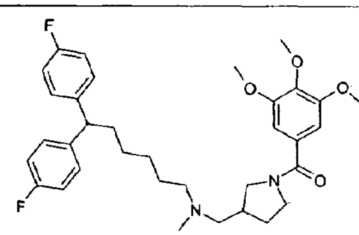 |

Figure 1

P/Q-type IC$_{50}$ = 4225 ± 1423nM (n=5)

N-type IC$_{50}$ = 198 ± 43nM (n=5)

L-type IC$_{50}$ >> 10μM (n=5) (estimate: 91μM)

Effect of P17 on Various Ca$^{2+}$ Channels

P/Q-type IC$_{50}$ = 4116 ± 327nM (n=5)
N-type IC$_{50}$ =133 ± 61nM (n=6)
L-type IC$_{50}$ > 10µM (n=5) (estimate :13.2 µM)

N-TYPE CALCIUM CHANNEL BLOCKERS

CROSS REFERENCE TO RELATED APPLICATIONS

This application claims priority under 35 U.S.C. § 119(e) to U.S. provisional application Ser. No. 60/474,864 field 30 May 2003, which is incorporated herein by reference.

TECHNICAL FIELD

The invention relates to compounds useful in treating conditions associated with calcium channel function. More specifically, the invention concerns compounds containing substituted or unsubstituted derivatives of 3-aminomethyl pyrrolidine-based compounds that are useful in treatment of conditions such as stroke and pain.

BACKGROUND ART

Native calcium channels have been classified by their electrophysiological and pharmacological properties as T, L, N, P and Q types (for reviews see McCleskey, E. W., et al., *Curr. Topics. Membr.* (1991) 39:295-326, and Dunlap, K., et al., *Trends Neurosci* (1995) 18:89-98). T-type (or low voltage-activated) channels describe a broad class of molecules that transiently activate at negative potentials and are highly sensitive to changes in resting potential. The L, N, P and Q-type channels activate at more positive potentials (high voltage activated) and display diverse kinetics and voltage-dependent properties. There is some overlap in biophysical properties of the high voltage-activated channels, consequently pharmacological profiles are useful to further distinguish them. L-type channels are sensitive to dihydropyridine agonists and antagonists, N-type channels are blocked by the Conus geographus peptide toxin, ω-conotoxin GVIA, and P-type channels are blocked by the peptide ω-agatoxin IVA from the venom of the funnel web spider, *Agelenopsis aperta*. A fourth type of high voltage-activated calcium channel (Q-type) has been described, although whether the Q- and P-type channels are distinct molecular entities is controversial (Sather, W. A., et al., *Neuron* (1995) 11:291-303; Stea, A., et al., *Proc. Natl. Acad. Sci. USA* (1994) 91:10576-10580; Bourinet, E., et al., *Nature Neuroscience* (1999) 2:407-415). Several types of calcium conductances do not fall neatly into any of the above categories and there is variability of properties even within a category suggesting that additional calcium channels subtypes remain to be classified.

Biochemical analyses show that neuronal high voltage activated calcium channels are heterooligomeric complexes consisting of at least three distinct subunits ($\alpha_1$, $\alpha_2\delta$ and $\beta$) (reviewed by De Waard, M., et al., *Ion Channels* (1997) vol. 4, Narahashi, T., ed., Plenum Press, NY). The $\alpha_1$ subunit is the major pore-forming subunit and contains the voltage sensor and binding sites for calcium channel antagonists. The mainly extracellular $\alpha_2$ is disulfide-linked to the transmembrane $\delta$ subunit and both are derived from the same gene and are proteolytically cleaved in vivo. The $\beta$ subunit is a nonglycosylated, hydrophilic protein with a high affinity of binding to a cytoplasmic region of the $\alpha_1$ subunit. A fourth subunit, $\gamma$, is unique to L-type calcium channels expressed in skeletal muscle T-tubules. The isolation and characterization of $\gamma$-subunit-encoding cDNA's is described in U.S. Pat. No. 5,386,025 which is incorporated herein by reference.

Recently, each of these $\alpha_1$ subtypes has been cloned and expressed, thus permitting more extensive pharmacological studies. These channels have been designated $\alpha_{1A}$-$\alpha_{1I}$ and $\alpha_{1S}$ and correlated with the subtypes set forth above. $\alpha_{1A}$ channels are of the P/Q type; $\alpha_{1B}$ represents N-type; $\alpha_{1C}$, $\alpha_{1D}$, $\alpha_{1F}$ and $\alpha_{1S}$ represent L-type; $\alpha_1$E represents a novel type of calcium conductance, and $\alpha_{1G}$-$\alpha_{1I}$ represent members of the T-type family, reviewed in Stea, A., et al., in *Handbook of Receptors and Channels* (1994), North, R. A. ed. CRC Press; Perez-Reyes, et al., *Nature* (1998) 391:896-900; Cribbs, L. L., et al., *Circulation Research* (1998) 83:103-109; Lee, J. H., et al., *Journal of Neuroscience* (1999) 19:1912-1921.

Further details concerning the function of N-type channels, which are mainly localized to neurons, have been disclosed, for example, in U.S. Pat. No. 5,623,051, the disclosure of which is incorporated herein by reference. As described, N-type channels possess a site for binding syntaxin, a protein anchored in the presynaptic membrane. Blocking this interaction also blocks the presynaptic response to calcium influx. Thus, compounds that block the interaction between syntaxin and this binding site would be useful in neural protection and analgesia. Such compounds have the added advantage of enhanced specificity for presynaptic calcium channel effects.

U.S. Pat. No. 5,646,149 describes calcium channel antagonists of the formula A-Y-B wherein B contains a piperazine or piperidine ring directly linked to Y. An essential component of these molecules is represented by A, which must be an antioxidant; the piperazine or piperidine itself is said to be important. The exemplified compounds contain a benzhydril substituent, based on known calcium channel blockers (see below). U.S. Pat. No. 5,703,071 discloses compounds said to be useful in treating ischemic diseases. A mandatory portion of the molecule is a tropolone residue; among the substituents permitted are piperazine derivatives, including their benzhydril derivatives. U.S. Pat. No. 5,428,038 discloses compounds which are said to exert a neural protective and antiallergic effect. These compounds are coumarin derivatives which may include derivatives of piperazine and other six-membered heterocycles. A permitted substituent on the heterocycle is diphenylhydroxymethyl. Thus, approaches in the art for various indications which may involve calcium channel blocking activity have employed compounds which incidentally contain piperidine or piperazine moieties substituted with benzhydril but mandate additional substituents to maintain functionality.

Certain compounds containing both benzhydril moieties and piperidine or piperazine are known to be calcium channel antagonists and neuroleptic drugs. For example, Gould, R. J., et al., *Proc. Natl. Acad. Sci. USA* (1983) 80:5122-5125 describes antischizophrenic neuroleptic drugs such as lidoflazine, fluspirilene, pimozide, clopimozide, and penfluridol. It has also been shown that fluspirilene binds to sites on L-type calcium channels (King, V. K., et al., *J Biol Chem* (1989) 264:5633-5641) as well as blocking N-type calcium current (Grantham, C. J., et al., *Brit J Pharmacol* (1944) 111:483-488). In addition, Lomerizine, as developed by Kanebo, K. K., is a known calcium channel blocker; Lomerizine is, however, not specific for N-type channels. A review of publications concerning Lomerizine is found in Dooley, D., *Current Opinion in CPNS Investigational Drugs* (1999) 1:116-125.

U.S. Pat. Nos. 6,011,035; 6,294,533; 6,310,059; and 6,387,897 describe selective N-type calcium channel blockers that were designed based on the recognition that the combination of a piperazine or piperidine ring coupled through a linker to a benzhydril moiety results in effective calcium channel blocking activity. The present invention is based on the observation that substitution of the piperazine or piperidine ring with 3-aminomethyl pyrrolidine results in unexpectedly high affinity for N-type calcium channels.

The compounds are useful for treating stroke, pain, anxiety and other calcium channel-associated disorders, as further described below. By focusing on these moieties, compounds useful in treating indications associated with calcium channel activity are prepared.

DISCLOSURE OF THE INVENTION

The invention relates to compounds useful in treating conditions such as stroke, anxiety, overactive bladder, inflammatory bowel disease, head trauma, migraine, chronic, neuropathic and acute pain, epilepsy, hypertension, cardiac arrhythmias, and other indications associated with calcium metabolism, including synaptic calcium channel-mediated functions. The compounds of the invention are benzhydril or partly saturated benzhydril derivatives of 3-substituted pyrrolidine with substituents which enhance the calcium channel blocking activity of the compounds. Thus, in one aspect, the invention is directed to compounds of formulas (1) and (2) and therapeutic methods that employ these compounds. The compounds of the invention are those of the formulas:

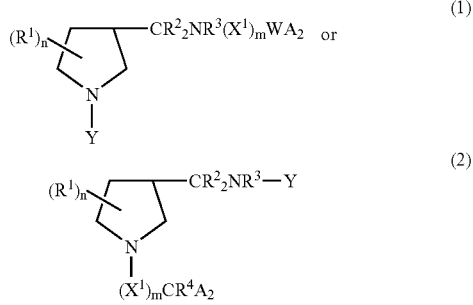

wherein:
Y is $(X^2)_lA$ or $(X^1)_mCR^4A_2$;
W is $CR^4$ or N;
$R^1$—$R^4$ are noninterfering substituents;
n is 0-7;
l and m are independently 0 or 1;
$X^1$-$X^2$ are linkers;
each A is independently a 5-7 membered optionally substituted aromatic or aliphatic ring optionally containing one or more heteroatoms selected from O, N and S.

The compounds of the invention may be in the form of a salt if appropriate or in the form of a prodrug. With respect to compounds of the invention that contain chiral centers (and each compound of the invention contains at least one chiral center) the compounds may be in the form of isolated stereoisomers or mixtures of various stereoisomers, including enantiomeric mixtures, equimolar mixtures of all possible stereoisomers, or various degrees of chiral or optical purity.

The linkers represented by $X^1$-$X^2$ are alkylene or alkenylene moieties optionally including one or more heteroatoms selected from N, O, and S and optionally containing the non interfering substitutions. The number of members in the chain in the linkers is 1-10.

Noninterfering substituents generally are independently optionally substituted alkyl (1-10C), alkenyl (2-10C), alkynyl (2-10C), aryl (5-12 ring members), arylalkyl (7-16C) or arylalkenyl (7-16C) each optionally having one or more C, generally 14C, replaced by heteroatoms (N, O and/or S) and wherein said optional substituents on alkyl, alkenyl, etc., may include one or more =O. Thus substituents include embodiments wherein these substituents may form an acyl, amide, or ester linkage with the atom to which it is bound. The substituents include, as well, one or more halo, $CF_3$, CN, OCF, $NO_2$, NO, SO, $SO_2$, $NR_2$, OR, SR, COOR, and/or $CONR_2$, wherein R is H or optionally substituted alkyl, alkenyl, alkynyl, aryl, arylalkyl, or arylalkenyl, as described above, and wherein S may be oxidized, and wherein two substituents may form a 3-7 membered saturated or unsaturated ring, said ring optionally itself substituted and optionally containing one or more heteroatoms (N, S, O). When a substituent shown in a formula is mandatory, it may also be H.

Thus, in some embodiments, non-interfering substituents in general include, but are not limited to, alkyl, alkenyl, alkynyl, aryl, arylalkyl, acyl, =O, halo, OR, $NR_2$, SR, —SOR, —$SO_2R$, —OCOR, —NRCOR, —$NRCONR_2$, —NRCOOR, —$OCONR_2$, —RCO, —COOR, $SO_2R$, $NRSOR$, $NRSO_2R$, —$SO_3R$, —$CONR_2$, $SO_2NR_2$, wherein each R is independently H or alkyl (1-8C), CN, $CF_3$, and $NO_2$, and like substituents.

The invention is directed to methods to antagonize calcium channel activity using the compounds of formulas (1) and (2) and thus to treat associated conditions. It will be noted that the conditions may be associated with undesired calcium channel activity, or the subject may have normal calcium channel function which nevertheless results in an undesirable physical or metabolic state. In another aspect, the invention is directed to pharmaceutical compositions containing these compounds.

The invention is also directed to combinatorial libraries containing the compounds of formulas (1) and (2) and to methods to screen these libraries for members containing particularly potent calcium channel blocking activity or for members that antagonize one type of such channels specifically.

BRIEF DESCRIPTION OF THE DRAWINGS

FIG. 1 shows the names and structures of illustrative compounds of the invention.

MODES OF CARRYING OUT THE INVENTION

Figure 2:
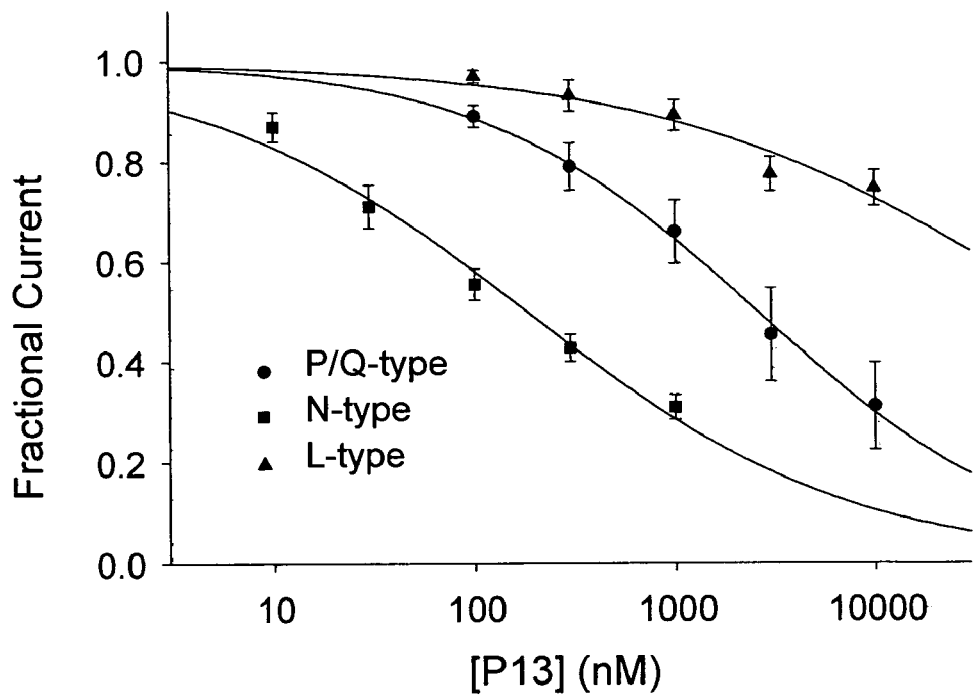
FIG. 2 is a graph showing the selectivity of compound P13 for N-, P/Q- and L-type channels.
Figure 3:
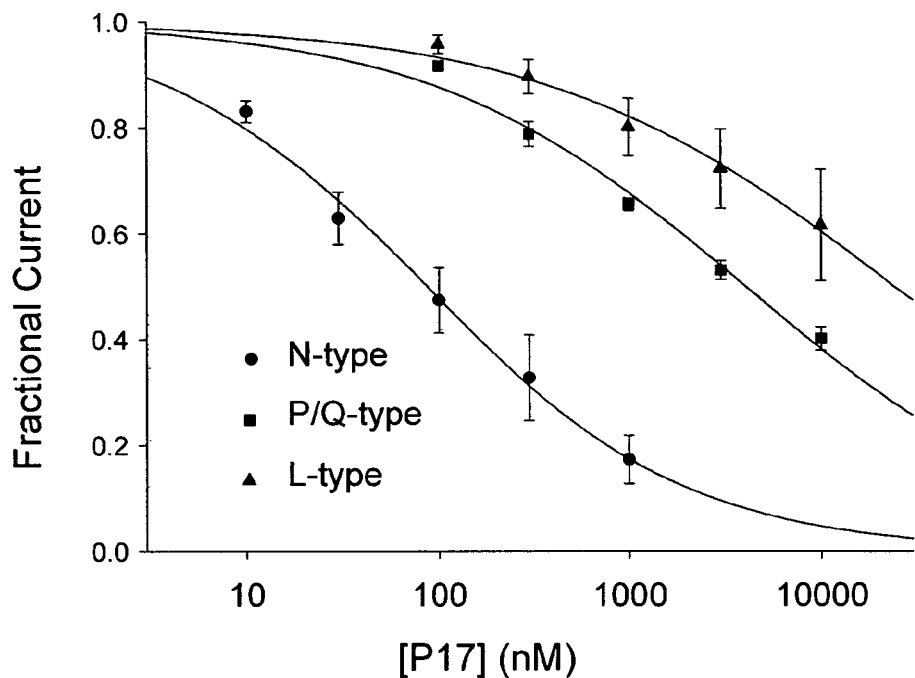
FIG. 3 is a graph showing the selectivity of compound P17 for N-, P/Q- and L-type channels.

The compounds of formulas (1) and (2), useful in the methods of the invention, exert their desirable effects through their ability to antagonize the activity of calcium channels. This makes them useful for treatment of certain conditions. Among such conditions are chronic pain conditions such as neuropathic pain, diabetic peripheral neuropathy, post-herpetic neuralgia, trigeminal neuralgia, AIDS related neuropathy, cancer pain, inflammatory pain, osteoarthritis pain, rheumatoid arthritis pain and fibromyalgia; acute pain; nociceptive pain; post-operative pain; mood disorders; anxiety disorders such as generalized anxiety disorder, social anxiety disorder, panic disorder, obsessive compulsive disorder and post-traumatic stress syndrome; depression; addiction disorders such as cocaine dependence and withdrawal, opioid dependence and withdrawal, alcohol dependence and withdrawal and nicotine dependence and withdrawal; gastrointestinal disorders such as inflammatory bowel disease and irritable bowel syndrome; and genitourinary disorders such as urinary incontinence, interstitial colitis and sexual dysfunction.

T-type calcium channels have been implicated in the following conditions: cardiovascular diseases such as hypertension, arrhythmias, atrial fibrillation congestive heart failure and angina pectoris; epilepsy conditions such as partial seizures, temporal lobe epilepsy, absence seizures, generalized seizures and tonic/clonic seizures; diabetes and cancer. T-type calcium channels are also involved in chronic pain conditions such as neuropathic pain, diabetic peripheral neuropathy, post-herpetic neuralgia, trigeminal neuralgia, AIDS related neuropathy, cancer pain, inflammatory pain, osteoarthritis pain, rheumatoid arthritis pain and fibromyalgia; acute pain; nociceptive pain and post-operative pain.

While the compounds of formulas (1) and (2) generally have this activity, the availability of a multiplicity of calcium channel blockers permits a nuanced selection of compounds for particular disorders. Thus, the availability of this class of compounds provides not only a genus of general utility in indications that are affected by calcium channel activity, but also provides a large number of compounds which can be mined and manipulated for specific interaction with particular forms of calcium channels. The availability of recombinantly produced calcium channels of the $\alpha_{1A}$-$\alpha_{1I}$ and $\alpha_{1S}$ types set forth above, facilitates this selection process. Dubel, S. J., et al., *Proc Natl Acad Sci USA* (1992) 89:5058-5062; Fujita, Y., et al., *Neuron* (1993) 10:585-598; Mikami, A., et al., *Nature* (1989) 340:230-233; Mori, Y., et al., *Nature* (1991) 350:398-402; Snutch, T. P., et al., *Neuron* (1991) 7:45-57; Soong, T. W., et al., *Science* (1993) 260:1133-1136; Tomlinson, W. J., et al., *Neuropharmacology* (1993) 32:1117-1126; Williams, M. E., et al., *Neuron* (1992) 8:71-84; Williams, M. E., et al., *Science* (1992) 257:389-395; Perez-Reyes, et al., *Nature* (1998) 391:896-900; Cribbs, L. L., et al., *Circulation Research* (1998) 83:103-109; Lee, J. H., et al., *Journal of Neuroscience* (1999) 19:1912-1921; McRory, J. E., et al., *Journal of Biological Chemistry* (2001) 276:3999-4011.

Thus, while it is known that calcium channel activity is involved in a multiplicity of disorders, the types of channels associated with particular conditions is the subject of ongoing data collection. For example, the association of N-type channels in conditions associated with neural transmission would indicate that compounds of the invention which target N-type channels are most useful in these conditions. Many of the members of the genus of compounds of formulas (1) and (2) exhibit high affinity for N-type and/or T-type channels; other members of the genus may preferentially target other channels.

There are three distinguishable types of calcium channel inhibition. The first, designated "open channel blockage," is conveniently demonstrated when displayed calcium channels are maintained at an artificially negative resting potential of about −100 mV (as distinguished from the typical endogenous resting maintained potential of about −70 mV). When the displayed channels are abruptly depolarized under these conditions, calcium ions are caused to flow through the channel and exhibit a peak current flow which then decays. Open channel blocking inhibitors diminish the current exhibited at the peak flow and can also accelerate the rate of current decay.

This type of inhibition is distinguished from a second type of block, referred to herein as "inactivation inhibition." When maintained at less negative resting potentials, such as the physiologically important potential of −70 mV, a certain percentage of the channels may undergo conformational change, rendering them incapable of being activated—i.e., opened—by the abrupt depolarization. Thus, the peak current due to calcium ion flow will be diminished not because the open channel is blocked, but because some of the channels are unavailable for opening (inactivated). "Inactivation" type inhibitors increase the percentage of receptors that are in an inactive state.

A third type of inhibition is designated "resting channel block." Resting channel block is the inhibition of the channel that occurs in the absence of membrane depolarization, that would normally lead to opening or inactivation. For example, resting channel blockers would diminish the peak current amplitude during the very first depolarization after drug application without additional inhibition during the depolarization.

In order to be maximally useful in treatment, it is also helpful to assess the side reactions which might occur. Thus, in addition to being able to modulate a particular calcium channel, it is desirable that the compound has very low activity with respect to the HERG $K^+$ channel which is expressed in the heart. Compounds that block this channel with high potency may cause reactions which are fatal. Thus, for a compound that modulates the calcium channel, it should also be shown that the HERG $K^+$ channel is not inhibited. Similarly, it would be undesirable for the compound to inhibit cytochrome p450 enzymes since these enzymes are required for drug detoxification. Finally, the compound will be evaluated for calcium ion channel type specificity by comparing its activity among the various types of calcium channels, and specificity for one particular channel type is preferred. The compounds which progress through these tests successfully are then examined in animal models as actual drug candidates.

The Invention Compounds

In the compounds of formulas (1) and (2), the following describes the nature of the various components.

The ring represented by A is preferably optionally substituted phenyl, cyclohexyl, 2-, 3- or 4-pyridyl, indolyl, 2- or 4-pyrimidyl, pyridazinyl, benzotriazolyl or benzimidazolyl. More preferably A is phenyl, cyclohexyl, pyridyl, or pyrimidyl. Most preferably A is cyclohexyl or phenyl. Each of these embodiments may optionally be substituted with a group defined herein such as optionally substituted alkyl, alkenyl, alkynyl, aryl, O-aryl, O-alkylaryl, O-aroyl, NR-aryl, N-alkylaryl, NR-aroyl, halo, OR, $NR_2$, SR, —OOCR, —NROCR, RCO, —COOR, —$CONR_2$, and/or $SO_2NR_2$, wherein each R is independently H or alkyl (1-8C), and/or by CN, $CF_3$, and/or $NO_2$, for example. Alkyl, alkenyl, alkynyl and aryl portions of these may be further substituted by similar substituents.

The rings represented by A may optionally be substituted with an inorganic substituent or an organic substituent comprising 15 non-hydrogen atoms or less. These substituents include optionally substituted alkyl (1-10C), optionally substituted alkenyl (2-10C), optionally substituted alkynyl (2-10C), an additional aryl moiety (5-12 ring members), arylalkyl, arylalkenyl or arylalkynyl (wherein aryl, alkyl, alkenyl and alkynyl are as defined above) and wherein in any of the foregoing, one or more carbons may be replaced by a heteroatom selected from O, S, and/or N. Each A may also independently and optionally be substituted by one or more inorganic moieties such as halo, nitro, sulfhydryl, hydroxyl, amino, or forms of OH, SH, or $NH_2$ wherein the H is replaced with optionally substituted organic moieties selected from those listed hereinabove. These moieties may in turn be further substituted as described. These substituents, specifically, may include =O.

Among preferred substituents on A are tert-butyl, methoxy, substituted alkoxy, hydroxy and halo.

Preferred embodiments of Y include those wherein A is phenyl ($\Phi$) or a partially saturated or fully saturated form thereof (Cy) such as $CH_2\Phi$, $CO\Phi$, $CH\Phi_2$, $CH_2CH_2X^4\Phi$, $COCH_2X^4\Phi$, $CH_2Cy$, $CH_2Cy_2$ and $CHCy\Phi$, wherein $X^4$ is C=O, $NR^3$, NCO, S, or O and where each $\Phi$ or Cy is unsubstituted or substituted with 1-3 substituents.

The 1-3 substituents are independently selected from halo, $CF_3$, OCF, lower alkyl (1-6C), lower aryl (6-10C) and arylalkyl (7-16C) optionally containing 1-4 heteroatoms (N, O, or S) and optionally substituted with inorganic substituents (comprising halo, N, P, O or S). Thus, these substituents may be, for example, halo, $NO_2$, $NR_2$, OR, SR, COR, COOR, $CONR_2$, NROCR, OOCR where R=H or alkyl (1-8C). Two substituents may form a 3-7 member ring optionally containing a heteroatom (N,S,O).

$R^1$ is a noninterfering substituent and n is 0-7, preferably 0-2, and most preferably 0-1. If n is 2 or 3, it is preferred that each $R^1$ occupy a different position on the pyrrolidine ring. Noninterfering substituents encompassed by $R^1$ include lower alkyl (1-6C), lower alkenyl (2-6C) and lower alkynyl (2-6C) optionally including one or more heteroatom selected from O, N and S, including substituted forms thereof comprising inorganic substituents such as halo, $NO_2$, $SO_2$, SO, NO and the like; $R^1$ may itself be one of these inorganic substituents. Two $R^1$ together one the same carbon may be =O or =NOH.

Preferred embodiments of $R^2$ include H, lower alkyl, lower alkenyl, and halo, preferably H or lower alkyl, and more preferably H. It is preferred that at least one of $R^2$ be H. Preferred embodiments of $R^3$ include H, lower alkyl, lower alkenyl, lower acyl, and these embodiments wherein one or more carbons is replaced with a heteroatom. Especially preferred for $R^3$ is H or $CONCH_2CH_3$.

Preferred embodiments for $R^4$ include H, alkyl, alkenyl, arylalkyl, arylalkenyl, hydroxy, alkoxy, sulfhydryl, alkylsulfhydryl, amino, and alkylamino. Especially preferred are H, hydroxy, and alkoxy.

$X^1$ may be present or absent (m is 0 or 1) and is a linker which spaces the benzhydril moiety from either the ring nitrogen or the nitrogen on the 3-aminomethyl substituent on the pyrrolidine. Typically, $X^1$ is an alkylene or alkenylene which is optionally substituted, wherein one particularly favored substitution is =O at the carbon adjacent the nitrogen to which $X^1$ is coupled. The alkylene or alkenylene chain may contain 1-10 members, preferably 1-8 members, more preferably 1-5 members and preferably is unsubstituted or contains a single substitution of =O at the carbon adjacent N. This chain, may also have one or more carbons replaced by a heteroatom, preferably N or O; preferably only a single heteroatom replaces a single carbon.

$X^2$ is defined as $X^1$; in general, $X^2$ contains an additional chain member as compared to $X^1$.

As used herein, the term "alkyl," "alkenyl" and "alkynyl" include straight-chain, branched-chain and cyclic monovalent substituents, containing only C and H when they are unsubstituted or unless otherwise noted. Examples include methyl, ethyl, isobutyl, cyclohexyl, cyclopentylethyl, 2-propenyl, 3-butynyl, and the like. Typically, the alkyl, alkenyl and alkynyl substituents contain 1-10C (alkyl) or 2-10C (alkenyl or alkynyl). Preferably they contain 1-6C (lower alkyl) or 2-6C (lower alkenyl or lower alkynyl).

Additional examples of optionally substituted alkyl groups include propyl, tert-butyl, etc., and including cycloalkyls such as cyclopropyl, cyclobutyl, cyclopentyl, cyclohexyl, cycloheptyl, etc.; examples of optionally substituted alkenyl groups include allyl, crotyl, 2-pentenyl, 3-hexenyl, 2-cyclopentenyl, 2-cyclohexenyl, 2-cyclopentenylmethyl, 2-cyclohexenylmethyl, etc.; $C_{1-4}$alkyl and alkenyl are preferred.

Heteroalkyl, heteroalkenyl and heteroalkynyl are similarly defined but may contain one or more O, S or N heteroatoms or combinations thereof within the backbone residue.

As used herein, "acyl" encompasses the definitions of alkyl, alkenyl, alkynyl, each of which is coupled to an additional residue through a carbonyl group. Heteroacyl includes the related heteroforms.

"Aromatic" moiety or "aryl" moiety refers to a monocyclic or fused bicyclic moiety such as phenyl or naphthyl; "heteroaromatic" also refers to monocyclic or fused bicyclic ring systems containing one or more heteroatoms selected from O, S and N. The inclusion of a heteroatom permits inclusion of 5-membered rings as well as 6-membered rings. Thus, typical aromatic/heteroaromatic systems include pyridyl, pyrimidyl, indolyl, benzimidazolyl, benzotriazolyl, isoquinolyl, quinolyl, benzothiazolyl, benzofuranyl, thienyl, furyl, pyrrolyl, thiazolyl, oxazolyl, imidazolyl and the like. Because tautomers are theoretically possible, phthalimido is also considered aromatic. Any monocyclic or fused ring bicyclic system which has the characteristics of aromaticity in terms of electron distribution throughout the ring system is included in this definition. Typically, the ring systems contain 5-12 ring member atoms.

Similarly, "arylalkyl" and "heteroarylalkyl" refer to aromatic and heteroaromatic systems which are coupled to another residue through a carbon chain, including substituted or unsubstituted, saturated or unsaturated, carbon chains, typically of 1-8C, or the hetero forms thereof. These carbon chains may also include a carbonyl group, thus making them able to provide substituents as an acyl or heteroacyl moiety.

In general, any alkyl, alkenyl, alkynyl, acyl, or aryl group contained in a substituent may itself optionally be substituted by additional substituents. The nature of these substituents is similar to those recited with regard to the primary substituents themselves. Thus, where an embodiment of a substituent is alkyl, this alkyl may optionally be substituted by the remaining substituents listed as substituents where this makes chemical sense, and where this does not undermine the size limit of alkyl per se; e.g., alkyl substituted by alkyl or by alkenyl would simply extend the upper limit of carbon atoms for these embodiments. However, alkyl substituted by aryl, amino, alkoxy, and the like would be included.

Examples of halogen include fluorine, chlorine, bromine, iodine, etc., with fluorine and chlorine preferred.

Examples of optionally substituted hydroxyl and thiol groups include optionally substituted alkyloxy or alkylthio (e.g., $C_{1-10}$alkyl) such as methyl, ethyl, propyl, isopropyl, butyl, isobutyl, sec-butyl, tert-butyl, pentyl, cyclopropyl, cyclobutyl, cyclopentyl, cyclohexyl, cycloheptyl, etc.); an optionally substituted arylalkyloxy or arylalkyl thio (e.g., phenyl-$C_{1-4}$alkyl, e.g., benzyl, phenylethyl, etc.). Where there are two adjacent hydroxyl or thiol substituents, the heteroatoms may be connected via an alkylene group such as $O(CH_2)_nO$ and $S(CH_2)_nS$ (where n=1-5). Examples include methylenedioxy, ethylenedioxy, etc. Oxides of thio-ether groups such as sulfoxides and sulfones are also envisioned.

Examples of optionally substituted hydroxyl groups also include optionally substituted $C_{2-4}$alkanoyl (e.g., acetyl, propionyl, butyryl, isobutyryl, etc.), $C_{1-4}$alkylsufonyl (e.g., methanesulfonyl, ethanesulfonyl, etc.) and an optionally substituted aromatic and heterocyclic carbonyl group including benzoyl, pyridinecarbonyl, etc.

Substituents on optionally substituted amino groups may bind to each other to form a cyclic amino group (e.g., 5- to 6-membered cyclic amino, etc., such as tetrahydropyrrole, piperazine, piperidine, pyrrolidine, morpholine, thiomorpholine, pyrrole, imidazole, etc.). Said cyclic amino group may have a substituent, and examples of the substituents include halogen (e.g., fluorine, chlorine, bromine, iodine, etc.), nitro, cyano, hydroxy group, thiol group, amino group, carboxyl group, an optionally halogenated $C_{1-4}$alkyl (e.g., trifluoromethyl, methyl, ethyl, etc.), an optionally halogenated $C_{1-4}$alkoxy (e.g., methoxy, ethoxy, trifluoromethoxy, trifluoroethoxy, etc.), $C_{2-4}$alkanoyl (e.g., acetyl, propionyl, etc.), $C_{1-4}$alkylsulfonyl (e.g., methanesulfonyl, ethanesulfonyl, etc.) the number of preferred substituents are 1 to 3.

An amino group may also be substituted once or twice (to form a secondary or tertiary amine) with a group such as an optionally substituted alkyl group including $C_{1-10}$alkyl (e.g., methyl, ethyl propyl etc.); an optionally substituted alkenyl group such as allyl, crotyl, 2-pentenyl, 3-hexenyl, etc., or an optionally substituted cycloalkyl group such as cyclopropyl, cyclobutyl, cyclopentyl, cyclohexyl, cycloheptyl, etc. In these cases, $C_{1-6}$alkyl, alkenyl and cycloalkyl are preferred. The amine group may also be optionally substituted with an aromatic or heterocyclic group, aralkyl (e.g., phenyl$C_{1-4}$alkyl) or heteroalkyl for example, phenyl, pyridine, phenylmethyl (benzyl), phenylethyl, pyridinylmethyl, pyridinylethyl, etc. The heterocyclic group may be a 5 or 6 membered ring containing 1-4 heteroatoms.

An amino group may be substituted with an optionally substituted $C_{2-4}$alkanoyl, e.g., acetyl, propionyl, butyryl, isobutyryl etc., or a $C_{1-4}$alkylsulfonyl (e.g., methanesulfonyl, ethanesulfonyl, etc.) or a carbonyl or sulfonyl substituted aromatic or heterocyclic ring, e.g., benzenesulfonyl, benzoyl, pyridinesulfonyl, pyridinecarbonyl etc. The heterocycles are as defined above.

Examples of optionally substituted carbonyl groups, or sulfonyl groups include optionally substituted forms of such groups formed from various hydrocarbyls such as alkyl, alkenyl and 5- to 6-membered monocyclic aromatic group (e.g., phenyl, pyridyl, etc.), as defined above.

The compounds of the invention may have ionizable groups so as to be capable of preparation as pharmaceutically acceptable salts. These salts may be acid addition salts involving inorganic or organic acids or the salts may, in the case of acidic forms of the compounds of the invention be prepared from inorganic or organic bases. Examples of inorganic bases with alkali metal hydroxides (e.g., sodium hydroxide, potassium hydroxide, etc.), alkaline earth metal hydroxides (e.g., of calcium, magnesium, etc.), and hydroxides of aluminum, ammonium, etc. Examples of organic bases include trimethylamine, triethylamine, pyridine, picoline, ethanolamine, diethanolamine, triethanolamine, dicyclohexylamine, N,N'-dibenzylethylenediamine, etc. Examples of inorganic acids include hydrochloric acid, hydrobromic acid, nitric acid, sulfuric acid, phosphoric acid, etc. Examples of organic acids include formic acid, oxalic acid, acetic acid, tartaric acid, methanesulfonic acid, benzenesulfonic acid, malic acid, methanesulfonic acid, benzenesulfonic acid, p-toluenesulfonic acid, etc. Also included are salts with basic amino acids such as arginine, lysine, ornithine, etc., and salts with acidic amino acids such as aspartic acid, glutamic acid, etc.

In addition, in some cases, the compounds of the invention contain one or more chiral centers. The invention includes the isolated stereoisomeric forms as well as mixtures of stereoisomers in varying degrees of chiral purity.

Synthesis of the Invention Compounds

The compounds of the invention may be synthesized using conventional methods. Illustrative of such methods are Schemes A, B, C, D, E, F, G and H.

Reaction Scheme A may be used to synthesize compounds of the invention such as P3, P4, P7, P8, P13, P14, P15, P17, P18, P19, P20, P21, P22, P24 and P25.

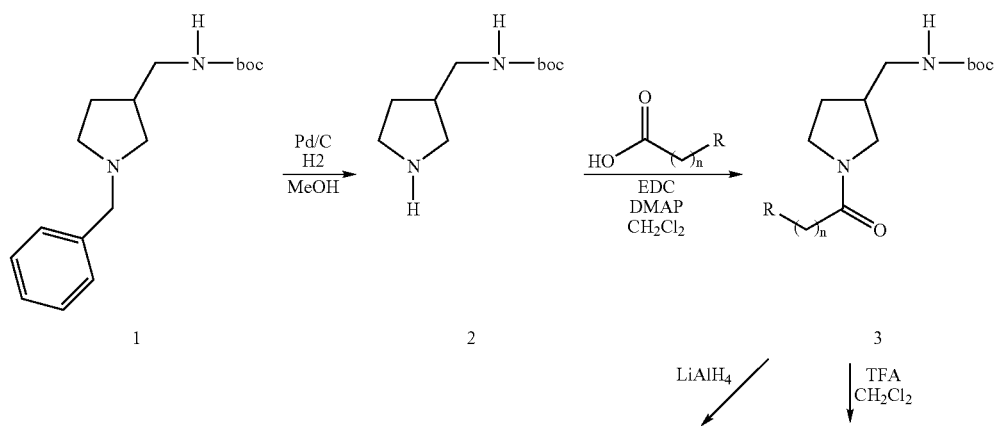

Reaction Scheme A

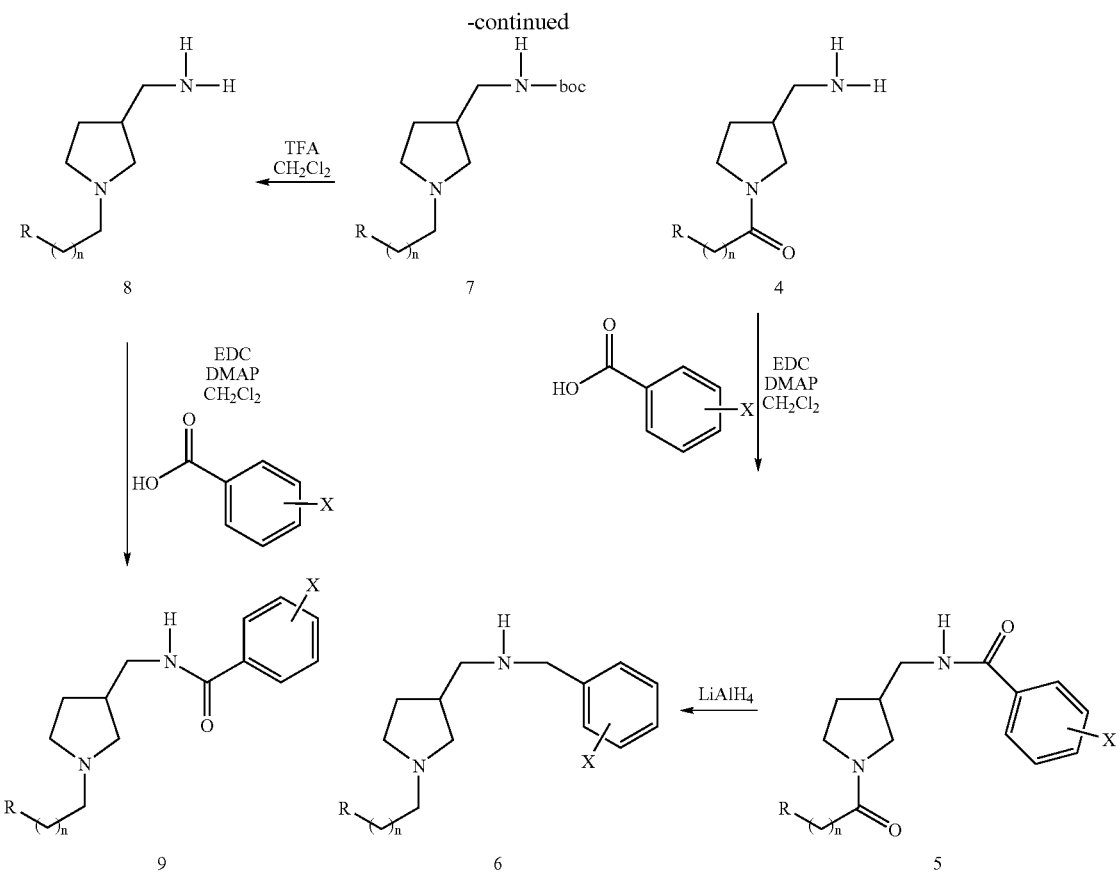

Treatment of commercially available (1-benzyl-pyrrolidin-3-ylmethyl)-carbamic acid tert-butyl ester (1) with Pd/C at 50 psi gives unprotected 3-aminomethyl-3-tert-butoxycarbonylpyrrolidine (2) in quantitative yield. Coupling of (2) with suitable carboxylic acid using EDC/DMAP in $CH_2Cl_2$ gives (3). Removal of BOC using TFA gives (4). Coupling of (4) with suitable benzoic acid derivatives under usual condition followed by reduction of amide with $LiAlH_4$ using aprotic solvent (THF) gives (6).

Reduction of amide (3) with $LiAlH_4$ followed by removal of BOC gives (8). Coupling of (8) with suitable benzoic acid derivatives gives (9).

Reaction Scheme B may be used to synthesize compounds of the invention such as P5, P6, P9, P10, P11, P12 and P23.

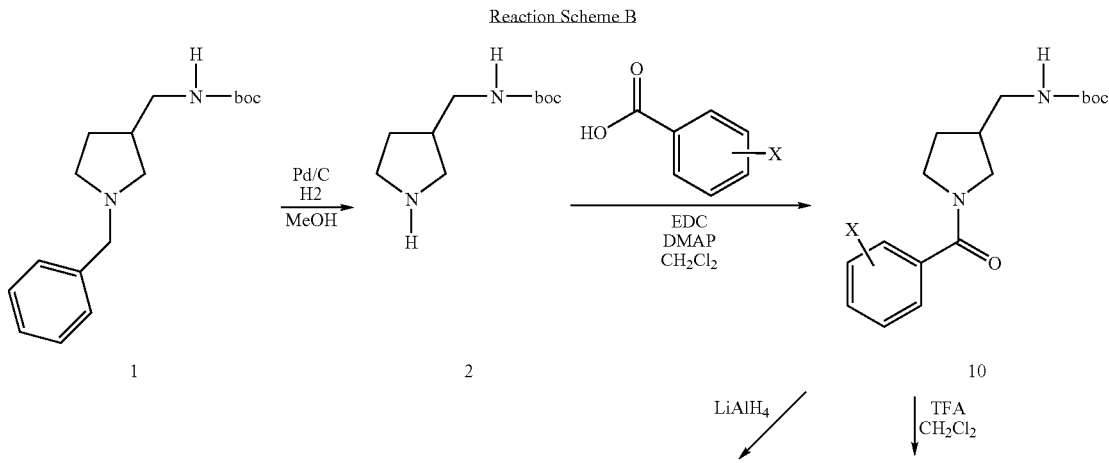

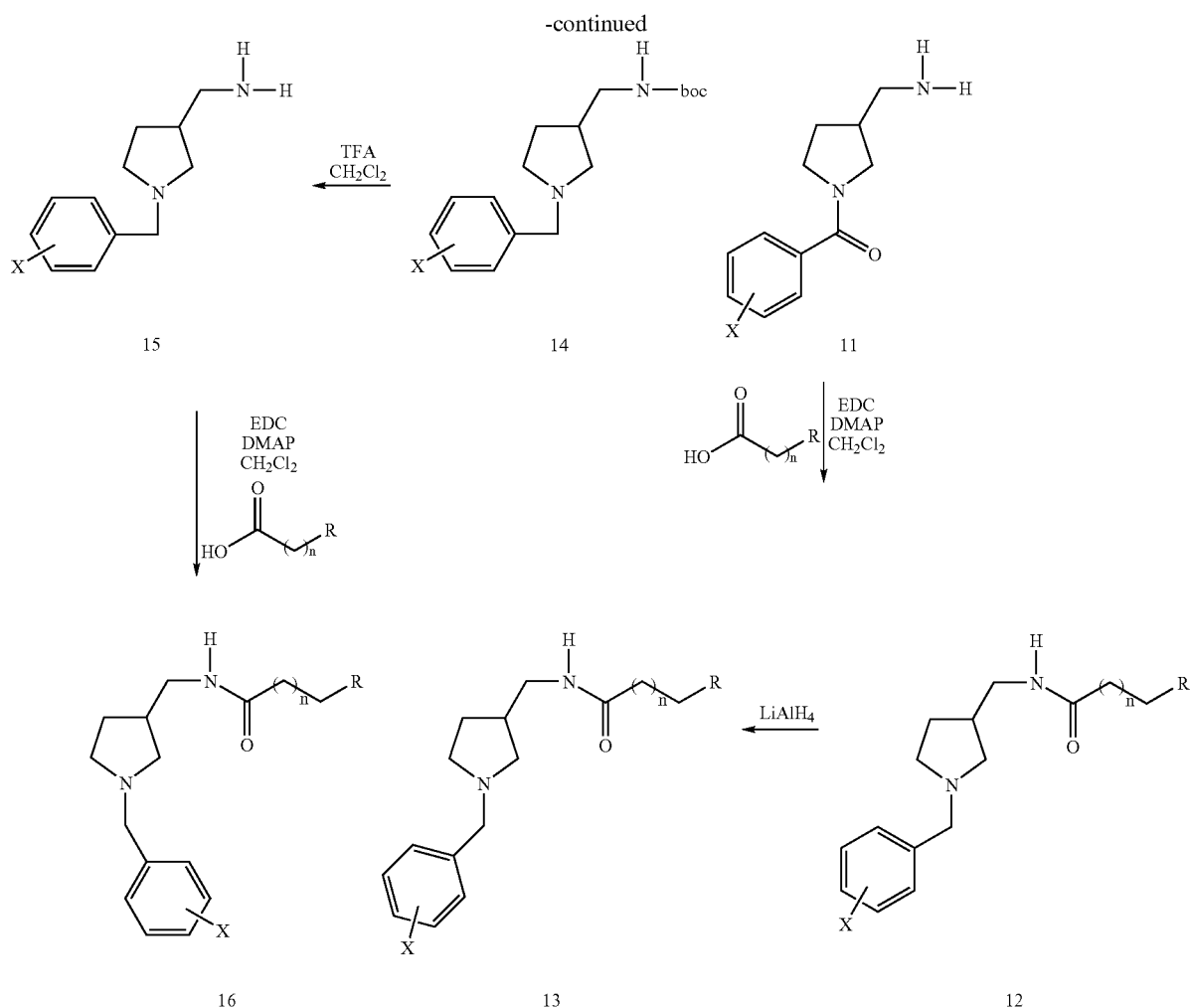

Treatment of (2) with suitable benzoic acid derivatives under usual condition (EDC/DMAP, $CH_2Cl_2$) followed by removal of BOC and coupling with suitable carboxylic acid and reduction of amide gives (13) in a good yield. Subsequently (10) was reduced followed by removal of BOC and coupling with carboxylic acid gives (16).

Reaction Scheme C may be used to synthesize compounds of the invention such as P1, P32, P37, P38 and P39.

Reaction Scheme C

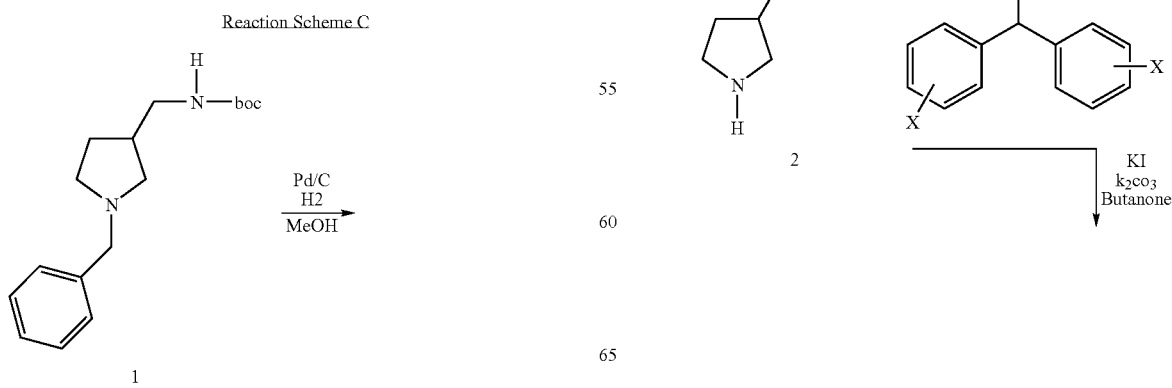

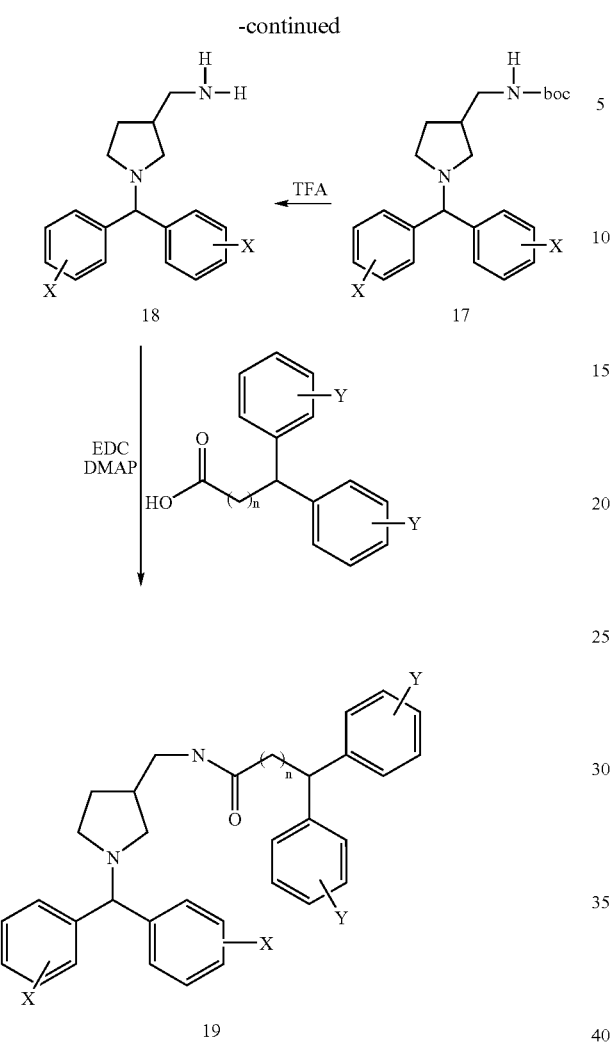
18 17
19
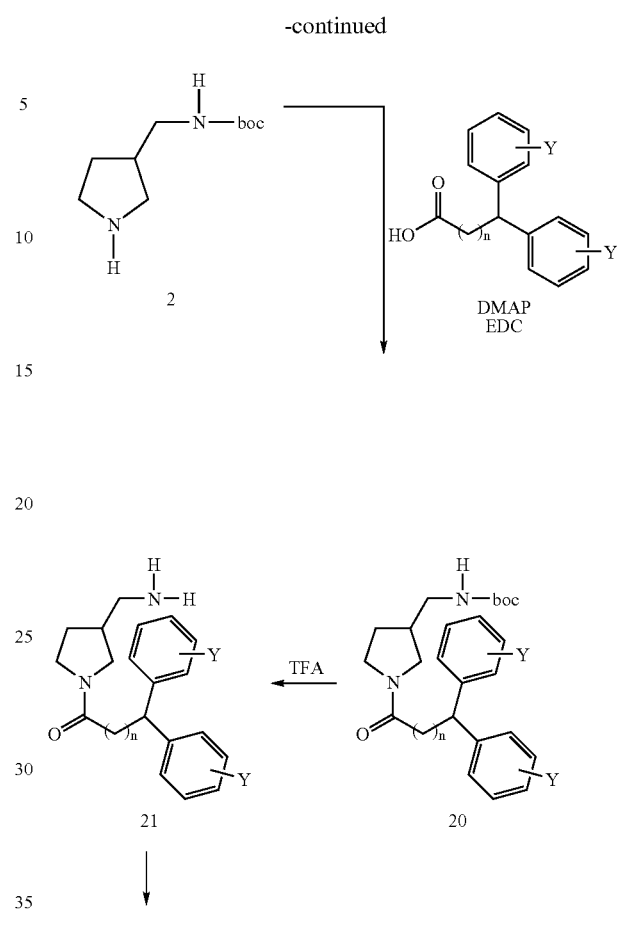
21 20
22
Treatment of (2) with chlorodiphenylmethane using KI/K₂CO₃/Butanone reflux overnight gives (17). Reaction of (17) with TFA followed by coupling with suitable carboxylic acid gives (19).
Reaction Scheme D may be used to synthesize compounds of the invention such as P2.
Reaction Scheme D
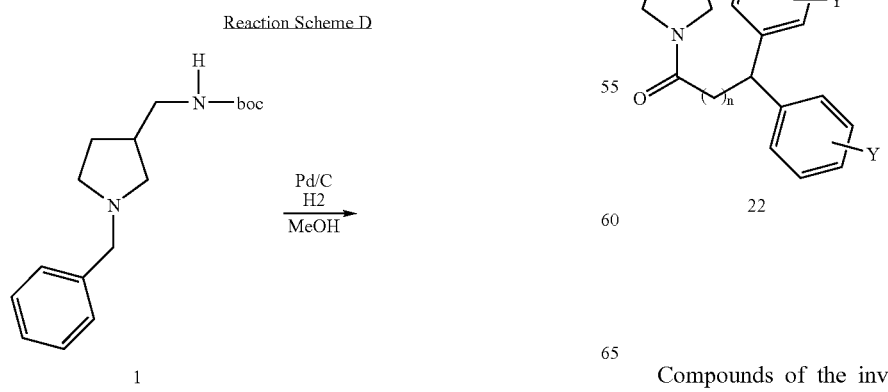
1
Compounds of the invention may also be synthesized using Reaction Scheme E.

Reaction Scheme E
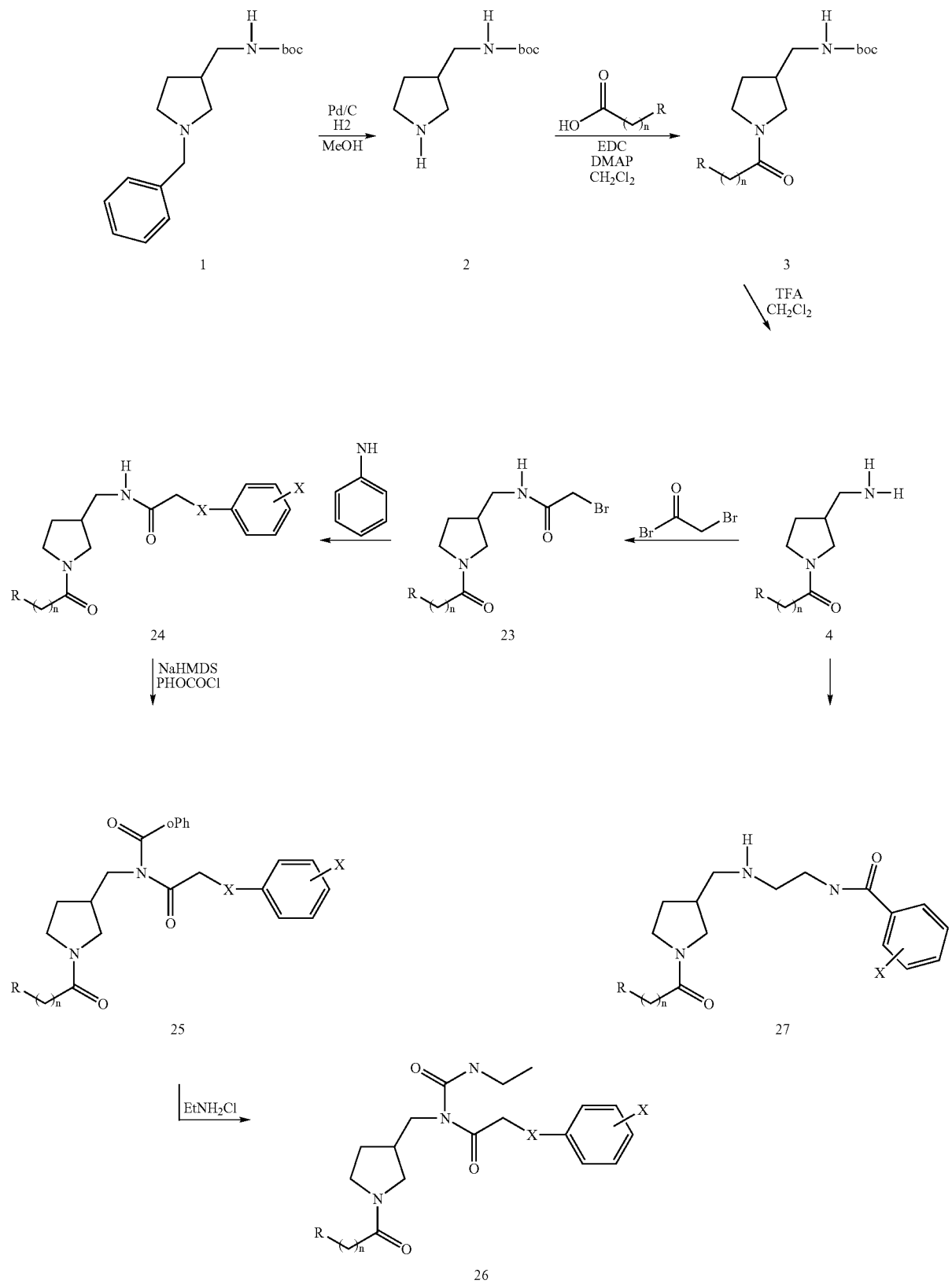

Compounds of the invention may also be synthesized using Reaction Scheme F.
Reaction Scheme F
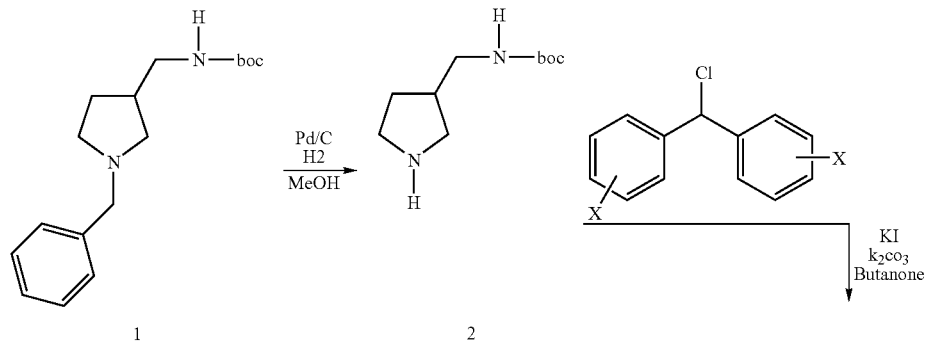
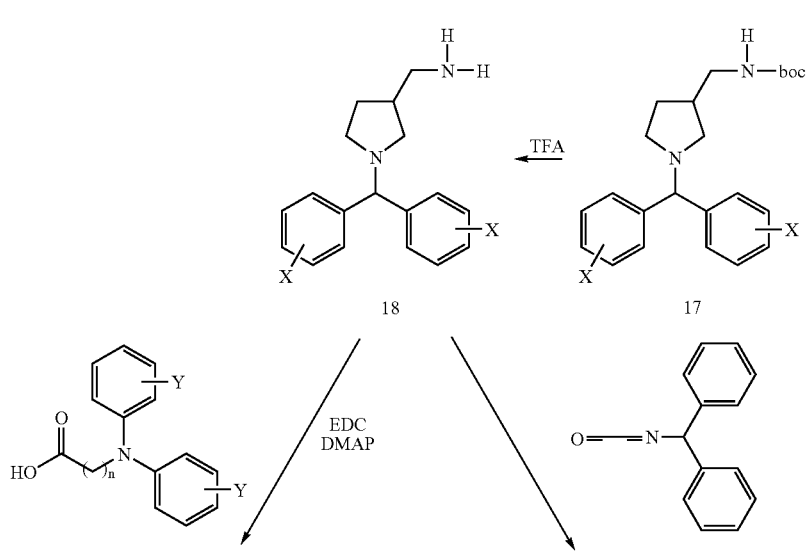
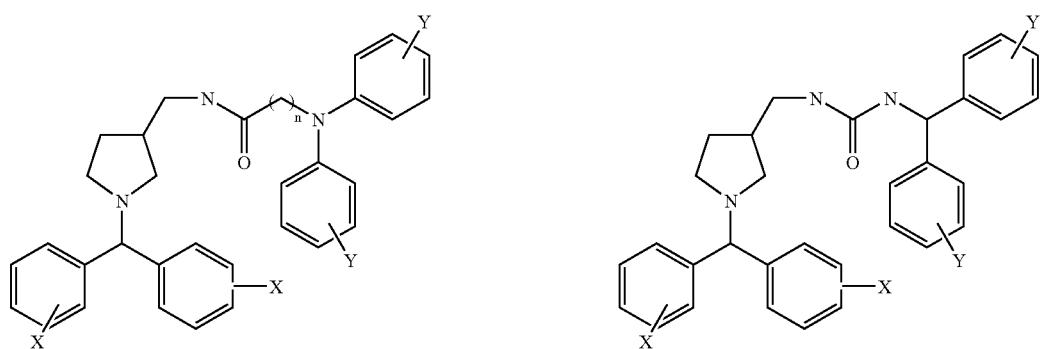

Compounds of the invention may also be synthesized using Reaction Scheme G.
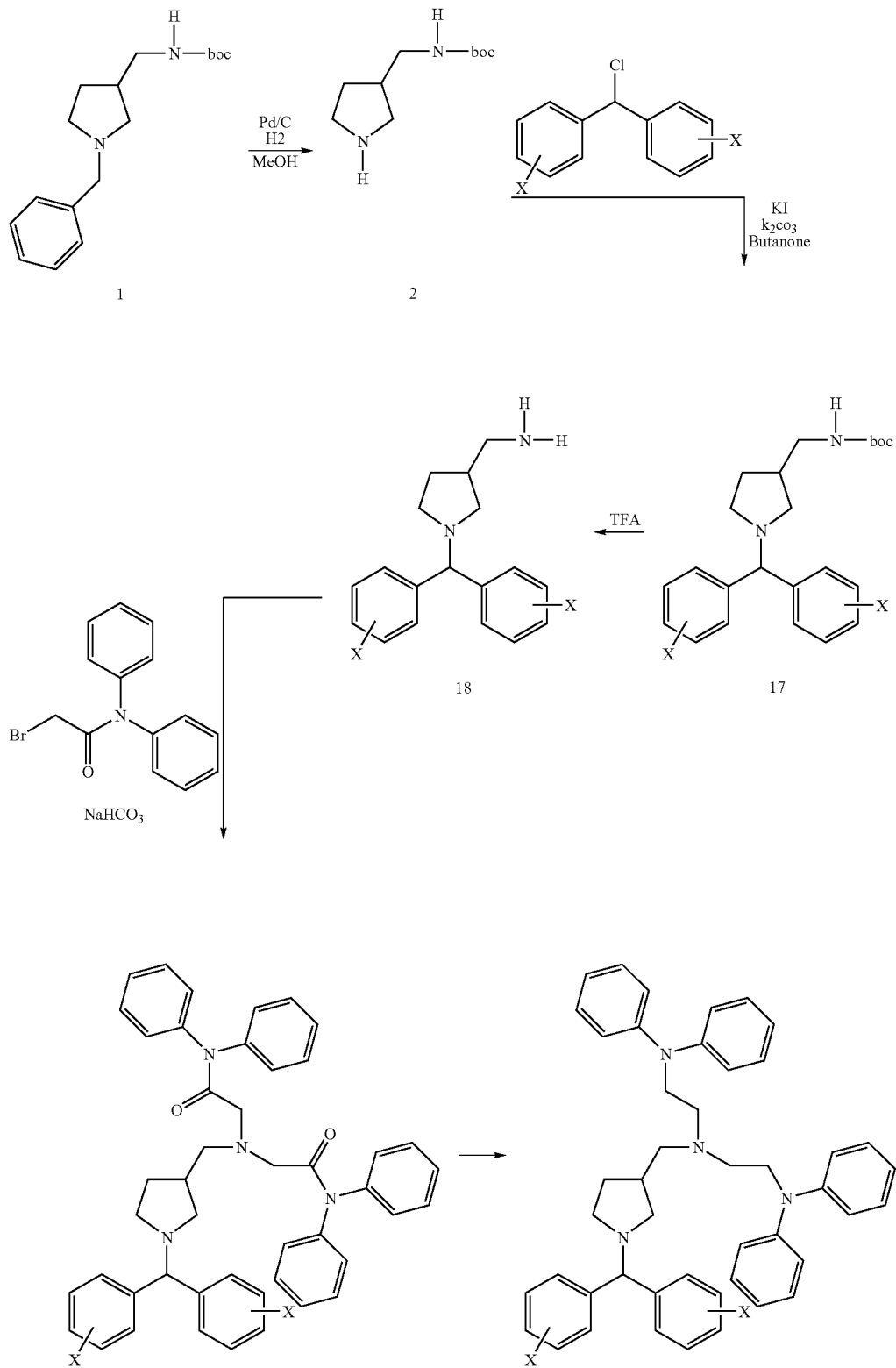
Reaction Scheme G Compounds of the invention may also be synthesized using Reaction Scheme H.
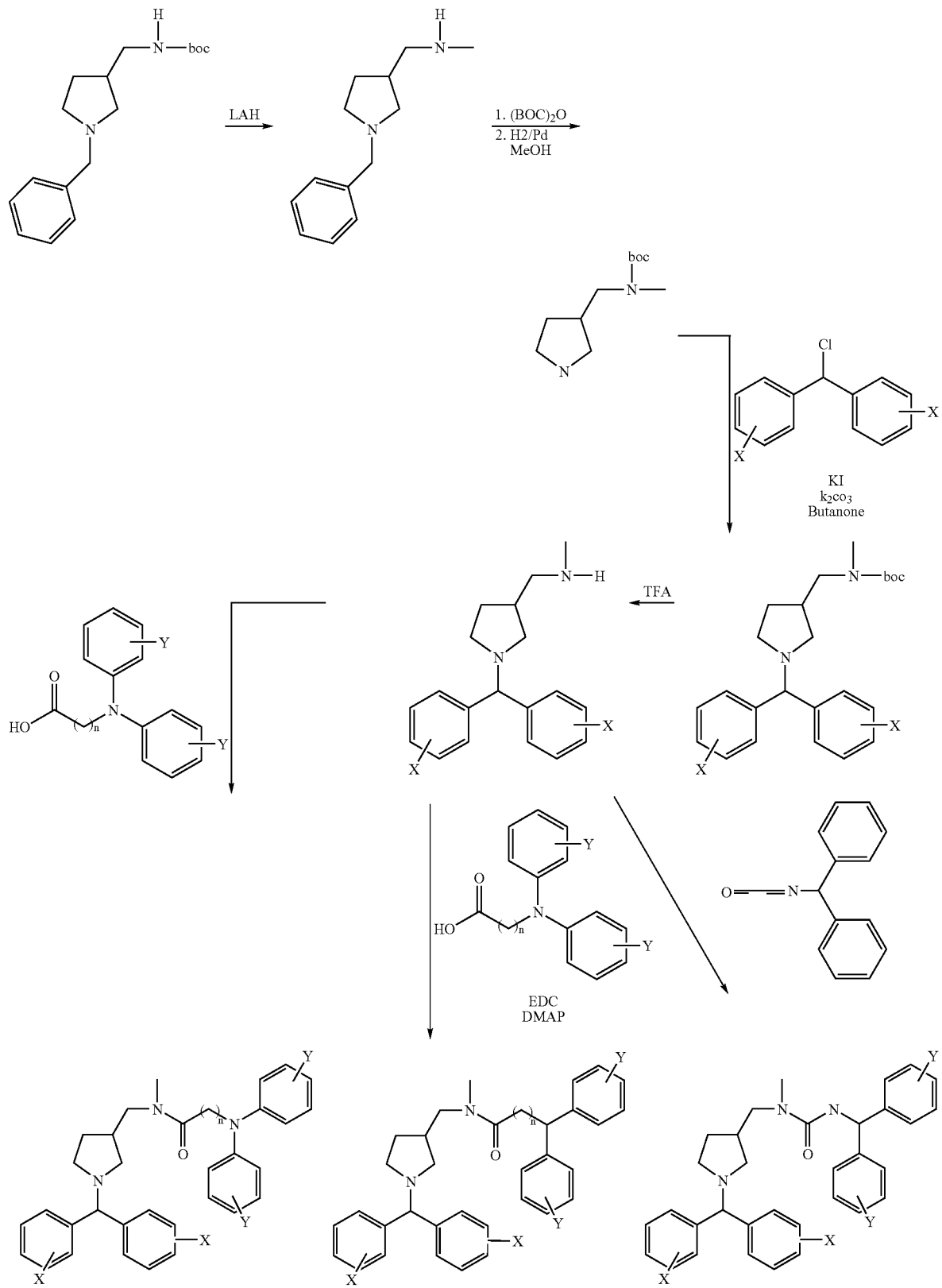
Reaction Scheme H Preferred Embodiments The compounds of formulas (1) and (2) are defined as shown in terms of the embodiments of their various substituents:

Particularly preferred embodiments of the compounds of formulas (1) and (2) are those wherein in CR⁴A₂ both A are phenyl; also included, however, are instances where one A is phenyl and the other is cyclohexyl, or both A are cyclohexyl.

Any of the A moieties contained in the compounds of formulas (1) and (2) may be substituted, as noted above. Preferred substituents include halo, especially fluoro, alkyl (1-6C), preferably methyl or t-butyl, OR, preferably methoxy, NR₂, preferably dimethylamino, diethylamino, methylamino or ethylamino, acetamido, CF₃, OCF₃ and the like. Two substituted positions may also form a ring. Preferably, where in CR⁴A₂ where both A are phenyl, the phenyl groups are identically substituted. Where one A is phenyl and the other is cyclohexyl, the combination of at least one substituent on the phenyl and an unsubstituted cyclohexyl is preferred. It is believed that halogenation of the compounds of the invention is helpful in modulating the in vivo half-life, and it may be particularly advantageous to include halogen substituents, such as fluoro substitutions on any phenyl moieties.

Illustrative compounds of the invention are represented by the following structures:

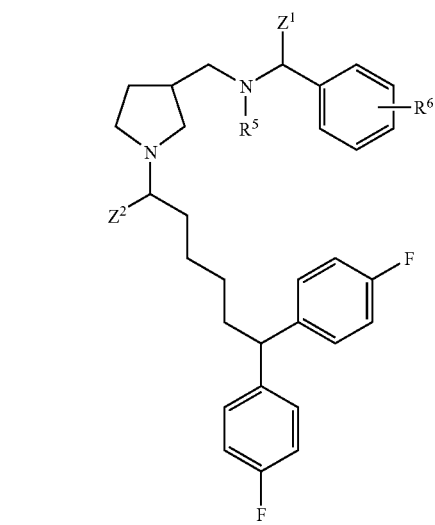
(3)

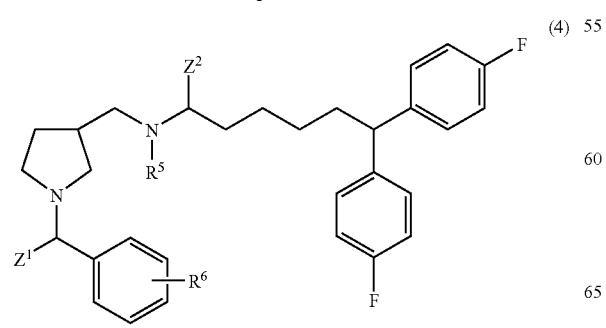
(4)

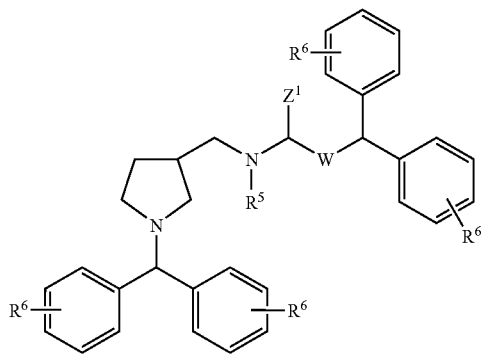
(5)

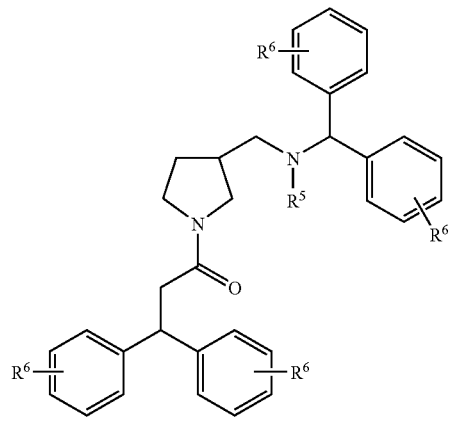
(6)

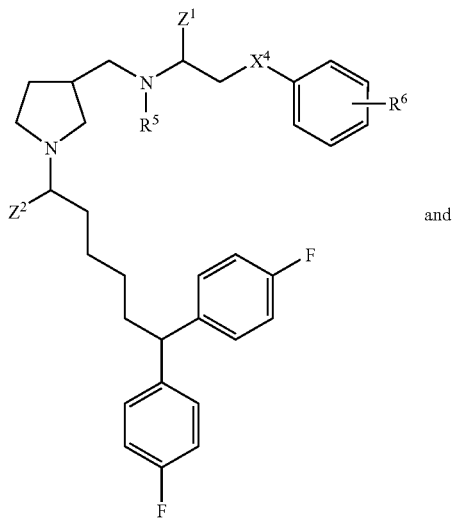
(7)

and

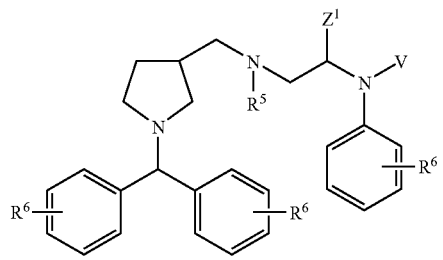
(8)

wherein:
each of Z¹ and Z² is independently either H₂ or =O;

$R^5$=H, optionally substituted alkyl, $(CR_2)_nCONR^7_2$, $(CR_2)_nNR^7_2$ where each $R^7$ is H, lower alkyl or aryl;
n=0-1;
V is alkyl or phenyl, each optionally substituted;
W is $CR_2$ or NR;
$X^4$=O, S, N or NCO; and
each of $R^6$ represents 0-3 substituents wherein the substituents are independently halo, $CF_3$, OCF, alkyl of 1-6C, aryl of (6-10C) or arylalkyl (7-16C) each optionally containing 1-4 heteroatoms (N, O, or S) and optionally substituted with inorganic substituents comprising N, P, O or S. Thus, $R^6$ may include substituents, for example, that are $NO_2$, $NR_2$, OR, SR, COR, COOR, $CONR_2$, NROCR, or OOCR, where each R=H or lower alkyl (1-4C). Two substituents may form a 3-7 member ring optionally containing a heteroatom (N,S, O).

The pattern of substitution will influence the strength of calcium channel blocking ability as well as specificity.

Libraries and Screening

The compounds of the invention can be synthesized individually using methods known in the art per se, or as members of a combinatorial library.

Synthesis of combinatorial libraries is now commonplace in the art. Suitable descriptions of such syntheses are found, for example, in Wentworth, Jr., P., et al., *Current Opinion in Biol* (1993) 9:109-115; Salemme, F. R., et al., *Structure* (1997) 5:319-324. The libraries contain compounds with various substituents and various degrees of unsaturation, as well as different chain lengths. The libraries, which contain, as few as 10, but typically several hundred members to several thousand members, may then be screened for compounds which are particularly effective against a specific subtype of calcium channel, i.e., the N-type channel. In addition, using standard screening protocols, the libraries may be screened for compounds which block additional channels or receptors such as sodium channels, potassium channels and the like.

Methods of performing these screening functions are well known in the art. Typically, the receptor to be targeted is expressed at the surface of a recombinant host cell such as human embryonic kidney cells. The ability of the members of the library to bind the channel to be tested is measured, for example, by the ability of the compound in the library to displace a labeled binding ligand such as the ligand normally associated with the channel or an antibody to the channel. More typically, ability to antagonize the receptor is measured in the presence of calcium, barium or other permanent divalent cation and the ability of the compound to interfere with the signal generated is measured using standard techniques.

In more detail, one method involves the binding of radiolabeled agents that interact with the calcium channel and subsequent analysis of equilibrium binding measurements including, but not limited to, on rates, off rates, $K_d$ values and competitive binding by other molecules. Another method involves the screening for the effects of compounds by electrophysiological assay whereby individual cells are impaled with a microelectrode and currents through the calcium channel are recorded before and after application of the compound of interest. Another method, high-throughput spectrophotometric assay, utilizes loading of the cell lines with a fluorescent dye sensitive to intracellular calcium concentration and subsequent examination of the effects of compounds on the ability of depolarization by potassium chloride or other means to alter intracellular calcium levels.

As described above, a more definitive assay can be used to distinguish inhibitors of calcium flow which operate as open channel blockers, as opposed to those that operate by promoting inactivation of the channel or as resting channel blockers. The methods to distinguish these types of inhibition are more particularly described in the examples below. In general, open-channel blockers are assessed by measuring the level of peak current when depolarization is imposed on a background resting potential of about −100 mV in the presence and absence of the candidate compound. Successful open-channel blockers will reduce the peak current observed and may accelerate the decay of this current. Compounds that are inactivated channel blockers are generally determined by their ability to shift the voltage dependence of inactivation towards more negative potentials. This is also reflected in their ability to reduce peak currents at more depolarized holding potentials (e.g., −70 mV) and at higher frequencies of stimulation, e.g., 0.2 Hz vs. 0.067 Hz. Finally, resting channel blockers would diminish the peak current amplitude during the very first depolarization after drug application without additional inhibition during the depolarization.

Utility and Administration

For use as treatment of human and animal subjects, the compounds of the invention can be formulated as pharmaceutical or veterinary compositions. Depending on the subject to be treated, the mode of administration, and the type of treatment desired—e.g., prevention, prophylaxis, therapy; the compounds are formulated in ways consonant with these parameters. A summary of such techniques is found in *Remington's Pharmaceutical Sciences*, latest edition, Mack Publishing Co., Easton, Pa., incorporated herein by reference.

In general, for use in treatment, the compounds of formulas (1) and (2) may be used alone, as mixtures of two or more compounds of formulas (1) and (2) or in combination with other pharmaceuticals. Depending on the mode of administration, the compounds will be formulated into suitable compositions to permit facile delivery.

Formulations may be prepared in a manner suitable for systemic administration or topical or local administration. Systemic formulations include those designed for injection (e.g., intramuscular, intravenous or subcutaneous injection) or may be prepared for transdermal, transmucosal, or oral administration. The formulation will generally include a diluent as well as, in some cases, adjuvants, buffers, preservatives and the like. The compounds can be administered also in liposomal compositions or as microemulsions.

For injection, formulations can be prepared in conventional forms as liquid solutions or suspensions or as solid forms suitable for solution or suspension in liquid prior to injection or as emulsions. Suitable excipients include, for example, water, saline, dextrose, glycerol and the like. Such compositions may also contain amounts of nontoxic auxiliary substances such as wetting or emulsifying agents, pH buffering agents and the like, such as, for example, sodium acetate, sorbitan monolaurate, and so forth.

Various sustained release systems for drugs have also been devised. See, for example, U.S. Pat. No. 5,624,677.

Systemic administration may also include relatively non-invasive methods such as the use of suppositories, transdermal patches, transmucosal delivery and intranasal administration. Oral administration is also suitable for compounds of the invention. Suitable forms include syrups, capsules, tablets, as is understood in the art.

For administration to animal or human subjects, the dosage of the compounds of the invention is typically 0.1-15 mg/kg, preferably 0.1-1 mg/kg. However, dosage levels are highly dependent on the nature of the condition, drug efficacy, the condition of the patient, the judgment of the practitioner, and the frequency and mode of administration.

The following preparations and examples are given to enable those skilled in the art to more clearly understand and to practice the present invention. They should not be considered as limiting the scope of the invention, but merely as being illustrative and representative thereof.

EXAMPLE 1

Synthesis of N-{1-[6,6-bis-(4-fluorophenyl)-hexanoyl]-pyrrolidin-3-ylmethyl}-3,4,5-trimethoxybenzamide

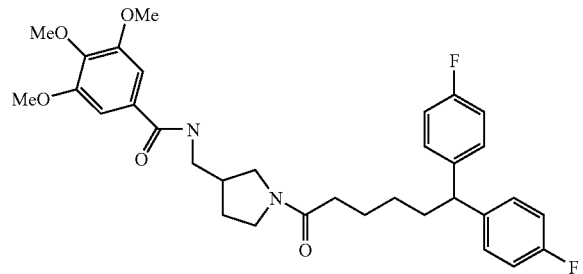

A. Synthesis of 3-aminomethyl-3-tert-butoxycarbonylpyrrolidine

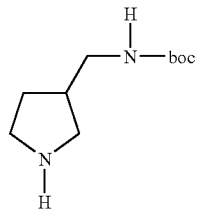

To a solution of (1-benzyl-pyrrolidin-3-ylmethyl)-carbamic acid tert-butyl ester (1) (3.0 g, 10.33 mmol) in CH$_3$OH (100 ml) was added Pd/C 20% (0.5 g). The resulting slurry was hydrogenated at 50 psi for 24 hours. The catalyst was filtered through Celite and filtrate evaporated under reduced pressure to give 2.0 g of desired product.

B. Synthesis of {1-[6,6-bis-(4-fluoro-phenyl)-hexanoyl]-pyrrolidin-3-ylmethyl}-carbamic acid tert-butyl ester

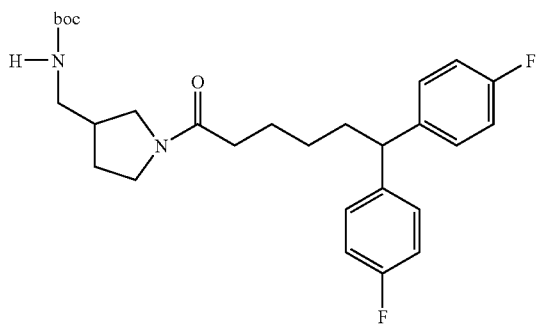

To a solution of 3-aminomethyl-3-tert-butoxycarbonylpyrrolidine (0.73 g, 3.65 mmol) in dry CH$_2$Cl$_2$ (40 ml) was added 5,5-bis-(4-fluorophenyl)-hexanoic acid (1.10 g, 3.65 mmol) under nitrogen. To the reaction was added EDC (1.4 g, 7.29 mmol) and DMAP (cat) and the reaction mixture stirred under nitrogen at room temperature overnight. The reaction was then concentrated under reduced pressure. The residue dissolved in ethyl acetate: water (10:1) (150 ml). The organic was washed with water (30 ml, 2×) and 10% NaOH (30 ml) and dried over MgSO$_4$ and evaporated to dryness. The resulting residue was purified by column chromatography using CH$_2$Cl$_2$:CH$_3$OH (15:1) to give 1.6 g of desired product.

C. Synthesis of 1-(3-aminomethyl-pyrrolidin-1-yl)-6,6-bis-(4-fluoro-phenyl)-hexan-1-one

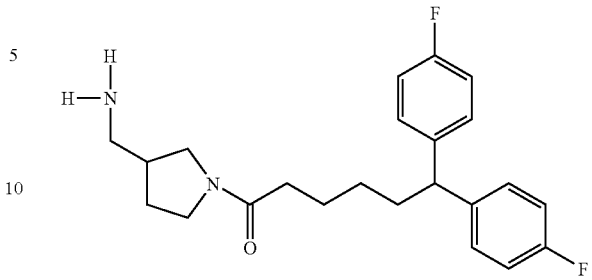

1-[6,6-bis-(4-Fluoro-phenyl)-hexanoyl]-pyrrolidin-3-ylmethyl}-carbamic acid tert-butyl ester (1.6 g, 3.29 mmol) was dissolved in dry CH$_2$Cl$_2$ (50 ml) followed by addition of TFA (20 ml). The resulting solution was stirred at room temperature for 2 hours. The solution was concentrated under reduced pressure. The resulting residue was dissolved in water (20 ml) and pH of the solution was adjusted to 10. The water phase was extracted with CH$_2$Cl$_2$ (100 ml), and dried over magnesium sulfate. The solvent was evaporated under reduced pressure to give the desired product in almost quantitative yield.

D. Final Product

To a solution of 1-(3-aminomethyl-pyrrolidin-1-yl)-6,6-bis-(4-fluoro-phenyl)-hexan-1-one (0.69 g, 1.78 mmol) in dry CH$_2$Cl$_2$ (40 ml) was added 3,4,5-trimethoxy benzoic acid (0.38 g, 1.78 mmol) under nitrogen. To the reaction was added EDC (0.68 g, 3.56 mmol) and DMAP (cat) and the reaction mixture stirred under nitrogen at room temperature overnight. The reaction was then concentrated under reduced pressure. The residue dissolved in ethyl acetate: water (10:1) (150 ml). The organic was washed with water (30 ml, 2×) and 10% NaOH (30 ml) and dried over MgSO$_4$ and evaporated to dryness. The resulting residue was purified by column chromatography using CH$_2$Cl$_2$:CH$_3$OH (15:1) to give a desired product in good yield

EXAMPLE 2

Synthesis of N-{1-[6,6-bis-(4-fluorophenyl)-hexanoyl]-pyrrolidin-3-ylmethyl}-3,4,5-trimethoxybenzamide

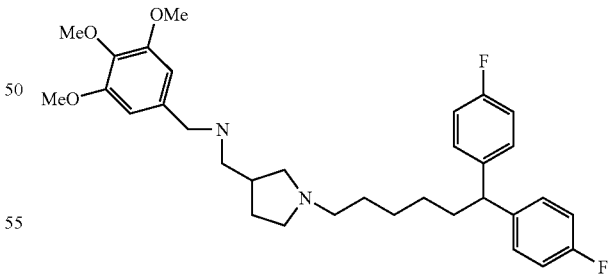

To solution of N-{1-[6,6-bis-(4-fluorophenyl)-hexanoyl]-pyrrolidin-3-ylmethyl}-3,4,5-trimethoxy-benzamide (0.75 g, 1.29 mmol) in dry THF (50 ml) was added LiAlH$_4$ (196 mg, 5.16 mmol) under nitrogen. The resulting suspension was stirred at room temperature for 24 hours. The reaction was quenched with EtOAc (15 ml) and extracted with water (20 ml, 2×) and 10% NaOH (20 ml), dried over MgSO$_4$ and evaporated. The resulting residue was purified by column chromatography using CH$_2$Cl$_2$:CH$_3$OH (15:1) to give 0.5 g of desired product.

EXAMPLE 3

Synthesis of N-{1-[6,6-bis-(4-fluorophenyl)-hexanoyl]-pyrrolidin-3-ylmethyl}-3,5-di-tert-butyl-4-methoxy-benzamide

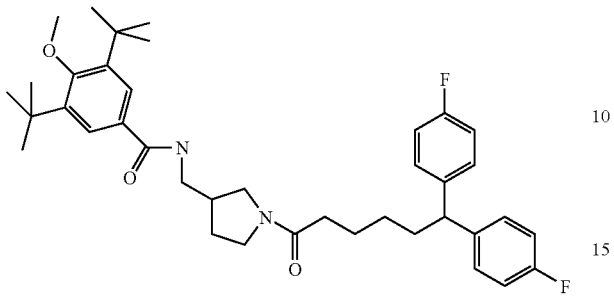

To a solution of 1-(3-aminomethyl-pyrrolidin-1-yl)-6,6-bis-(4-fluoro-phenyl)-hexan-1-one (0.49 g, 1.26 mmol) in dry CH$_2$Cl$_2$ (35 ml) was added 3,5-di-tert-butyl-4-methoxy benzoic acid (0.33 g, 1.26 mmol) under nitrogen. To the reaction was added EDC (0.48 g, 2.52 mmol) and DMAP (cat) and the reaction mixture stirred under nitrogen at room temperature overnight. The reaction was then concentrated under reduced pressure. The residue dissolved in ethyl acetate: water (10:1) (130 ml). The organic was washed with water (30 ml, 2×) and 10% NaOH (30 ml) and dried over MgSO$_4$ and evaporated to dryness. The resulting residue was purified by column chromatography using CH$_2$Cl$_2$:CH$_3$OH (15:1) to give a desired product in good yield.

EXAMPLE 4

Synthesis of N-(1-Benzhydryl-pyrrolidin-3-ylmethyl)-3,3-diphenyl-propionamide

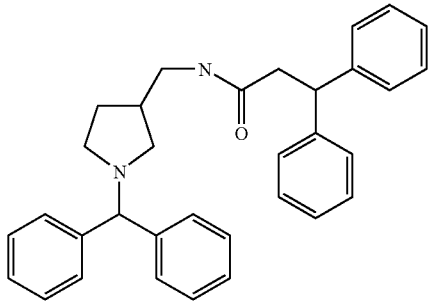

A. Synthesis of N-[1-benzhydryl]-3-aminomethyl-3-tert-butoxycarbonylpyrrolidine

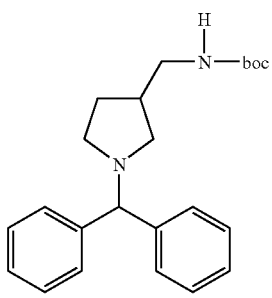

To a solution of chlorodiphenylmethane (0.68 g, 3.39 mmol) in butanone (15 ml) was added 3-aminomethyl-3-tert-butoxycarbonylpyrrolidine (0.68 g, 3.39 mmol), K$_2$CO$_3$ (0.56 g, 4.07 mmol) and KI (0.56, 3.39 mmol). The mixture was heated under reflux for 18 hours, then filtered and the solvent was removed in vacuo. The residue was dissolved in CH$_2$Cl$_2$ (50 ml) and washed with water (10 ml). Drying over MgSO$_4$ and removal of solvent under reduced pressure followed by column chromatography using Hex:EtOAc (3:1) gives the desired product.

B. Synthesis of C-(1-Benzhydryl-pyrrolidin-3-yl)-methylamine

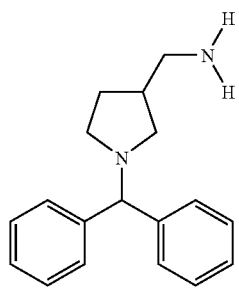

N-[1-Benzhydryl]-3-aminomethyl-3-tert-butoxycarbonylpyrrolidine (0.47 g, 1.28 mmol) was dissolved in dry CH$_2$Cl$_2$ (15 ml) followed by addition of TFA (8 ml). The resulting solution was stirred at room temperature for 2 hours. The solution was concentrated under reduced pressure. The resulting residue was dissolved in water (12 ml) and pH of the solution was adjusted to 10. The water phase was extracted with CH$_2$Cl$_2$ (100 ml), and dried over magnesium sulfate. The solvent was evaporated under reduced pressure to give the desired product in almost quantitative yield.

C. Final Product

To a solution of C-(1-Benzhydryl-pyrrolidin-3-yl)-methylamine (0.26 g, 0.98 mmol) in dry CH$_2$Cl$_2$ (25 ml) was added 3,3-diphenylpropionic acid (0.22 g, 0.98 mmol) under nitrogen. To the reaction was added EDC (0.37 g, 1.95 mmol) and DMAP (cat) and the reaction mixture stirred under nitrogen at room temperature overnight. The reaction was then concentrated under reduced pressure. The residue dissolved in ethyl acetate: water (10:1) (100 ml). The organic was washed with water (20 ml, 2×) and 10% NaOH (20 ml) and dried over MgSO$_4$ and evaporated to dryness. The resulting residue was purified by column chromatography using CH$_2$Cl$_2$:CH$_3$OH (15:1) to give a desired product in good yield

EXAMPLE 5

Synthesis of 1-{3-[Benzhydryl-amino)-methyl]-pyrrolidin-1-yl}-3,3-diphenyl-propan-1-one

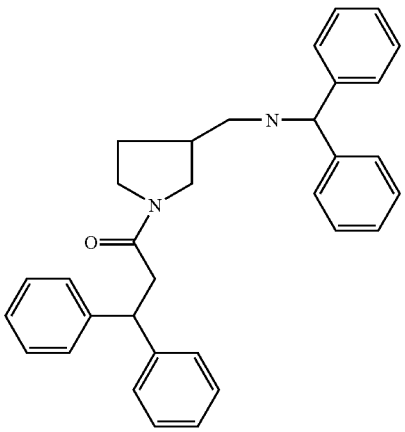

A. Synthesis of [1-(3,3-Diphenyl-propionyl)-pyrrolidin-3-ylmethy-carbamic acid tert-butyl ester

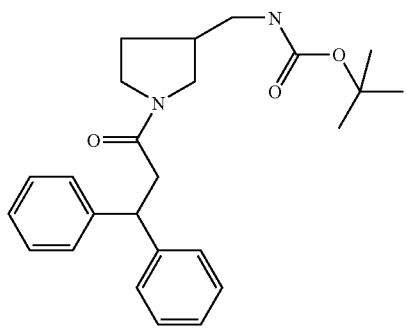

To a solution of 3-aminomethyl-3-tert-butoxycarbonylpyrrolidine (0.6 g, 2.99 mmol) in dry CH$_2$Cl$_2$ (30 ml) was added 3,3 diphenylpropionic acid (0.68 g, 2.99 mmol) under nitrogen. To the reaction was added EDC (1.15 g, 5.99 mmol) and DMAP (cat) and the reaction mixture stirred under nitrogen at room temperature overnight. The reaction was then concentrated under reduced pressure. The residue dissolved in ethyl acetate: water (10:1) (100 ml). The organic was washed with water (20 ml, 2×) and 10% NaOH (20 ml) and dried over MgSO$_4$ and evaporated to dryness. The resulting residue was purified by column chromatography using CH$_2$Cl$_2$:CH$_3$OH (15:1) to give 1.0 g of desired product.

B. Synthesis of 1-(3-Aminomethyl-pyrrolidin-1-yl)-3,3-diphenyl-propan-1-one

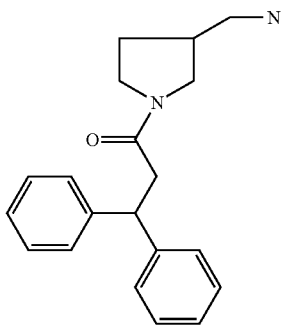

[1-(3,3-Diphenyl-propionyl)-pyrrolidin-3-ylmethy-carbamic acid tert-butyl ester (1.04 g, 2.54 mmol) was dissolved in dry CH$_2$Cl$_2$ (15 ml) followed by addition of TFA (10 ml). The resulting solution was stirred at room temperature for 2 hours. The solution was concentrated under reduced pressure. The resulting residue was dissolved in water (15 ml) and pH of the solution was adjusted to 10. The water phase was extracted with CH$_2$Cl$_2$ (100 ml), and dried over magnesium sulfate. The solvent was evaporated under reduced pressure to give the desired product in almost quantitative yield

C. Final Product

A solution of 1-(3-aminomethyl-pyrrolidin-1-yl)-3,3-diphenyl-propan-1-one (0.91 g, 2.95 mmol) and benzophenone (0.22 g, 1.18 mmol) was refluxed in benzene (20 ml) in the presence of p-toluenesulfonic acid (cat.) in a Dean-Stark overnight. Benzene was then removed and the residue extracted with EtOAc (40 ml). The organic phase was then washed with water (20 ml) and dried over MgSO$_4$. Removal of the solvent gave 0.9 g of crude intermediate which then dissolved in EtOH (15 ml) and NaBH$_4$ (0.93 g, 24.7 mmol) was gradually added to stirred solution. The reaction mixture was stirred overnight. EtOH was evaporated and residue was extracted with EtOAc, washed with water and dried. The resulting residue was purified by column chromatography using CH$_2$Cl$_2$:CH$_3$OH (15:1) to give desired product in 65% yield.

EXAMPLE 6

Synthesis of N-(1-Benzhydryl-pyrrolidin-3-ylmethyl)-2-diphenylamino-acetamide

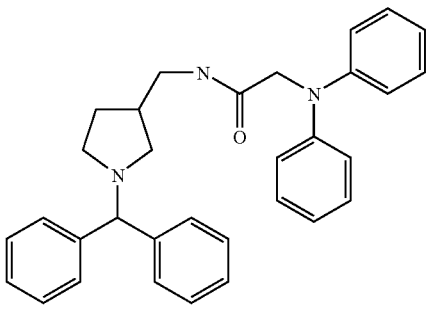

To a solution of C-(1-benzhydryl-pyrrolidin-3-yl)-methylamine (0.26 g, 0.97 mmol) in dry CH$_2$Cl$_2$ (20 ml) was added diphenylaminoacetic acid (0.22 g, 0.97 mmol) under nitrogen. To the reaction was added EDC (0.37 g, 1.95 mmol) and DMAP (cat) and the reaction mixture stirred under nitrogen at room temperature overnight. The reaction was then concentrated under reduced pressure. The residue dissolved in ethyl acetate: water (10:1) (100 ml). The organic was washed with water (25 ml, 2×) and 10% NaOH (25 ml) and dried over MgSO$_4$ and evaporated to dryness. The resulting residue was purified by column chromatography using hexane:ethyl acetate (3:1) to give the desired product in 75% yield.

EXAMPLE 7

Synthesis of 1-Benzhydryl-3-(1-benzhydryl-pyrrolidin-3-ylmethyl)-urea

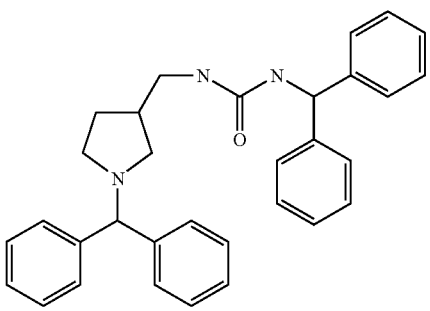

To a solution of C-(1-benzhydryl-pyrrolidin-3-yl)-methylamine (0.26 g, 0.97 mmol) in dry CH$_2$Cl$_2$ (5 ml) was added diphenylmethyl isocyanate (0.18 ml, 0.97 mmol) drop wise under nitrogen. The resulting mixture was stirred at room temperature over night. Removal of solvent under reduced pressure followed by column chromatography using CH$_2$Cl$_2$: CH$_3$OH (20:1) gives the desired product in 80% yield.

EXAMPLE 8

Synthesis of 2-{(1-Benzhydryl-pyrrolidin-3-ylmethyl)-[(diphenylcarbamoyl)-methyl]-amino}-N,N-diphenyl-acetamide

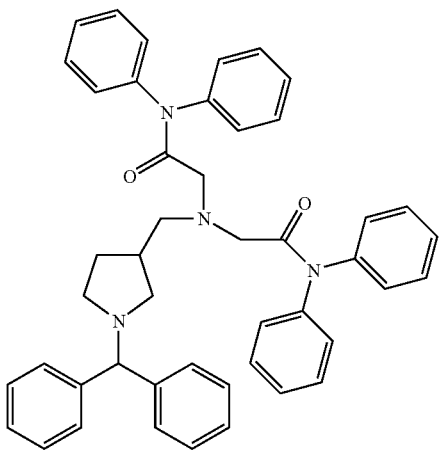

To a solution of C-(1-benzhydryl-pyrrolidin-3-yl)-methylamine (0.26 g, 0.97 mmol) in dry $CH_3CN$ (10 ml) was added 2-bromo-N,N-diphenyl acetamide (0.56 g, 1.94 mmol) and $NaHCO_3$ (0.17 g, 1.95 mmol) under nitrogen. The reaction mixture was refluxed over night. After cooling, the solvent was evaporated and residue was taken up with water (5 ml) and extracted with $CHCl_3$ (3×25 ml). The organic was dried over $MgSO_4$ and evaporated to dryness. The resulting residue was purified by column chromatography using $CH_2Cl_2:CH_3OH$ (15:1) to give the desired product in 82% yield.

EXAMPLE 9

Synthesis of N-(1-Benzhydryl-pyrrolidin-3-ylmethyl)-N-(2-diphenylamino-ethyl)-N'N'-diphenyl-ethane-1,2-diamine

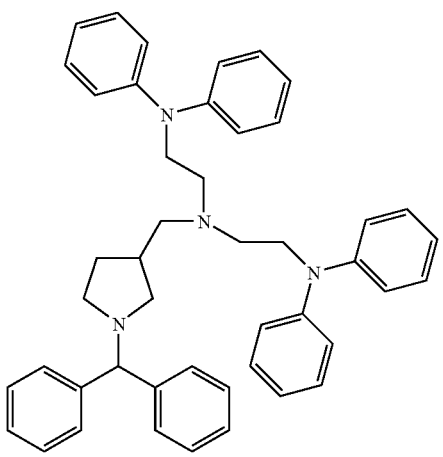

To a solution of 2-{(1-benzhydryl-pyrrolidin-3-ylmethyl)-[(diphenylcarbamoyl)-methyl]-amino}-N,N-diphenyl-acetamide (0.39 g, 0.57 mmol) in dry THF (10 ml) was added $BH_3$-THF (2.5 ml, 2.29 mmol) slowly. The reaction mixture was then refluxed overnight. It was then cooled and methanol was added slowly to decompose excess $BH_3$. Solvent removed and 10% HCl in methanol (20 ml) was added and refluxed for 1 hr. Cooled and solid $NaHCO_3$ added until neutral. Methanol was removed and extracted with ethyl acetate. The organic was dried over $MgSO_4$ and evaporated to dryness. The resulting residue was purified by column chromatography using hexane:ethyl acetate (11:1) to give the desired product in 80% yield.

EXAMPLE 10

Synthesis of N-(1-Benzhydryl-pyrrolidin-3-ylmethyl)-N-methyl-3,3-diphenyl-propionamide

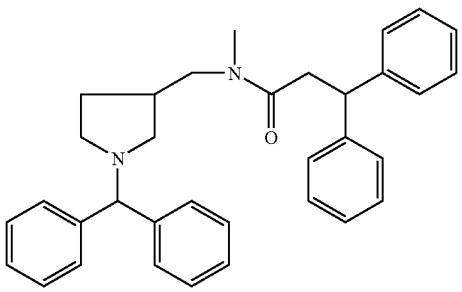

A. Synthesis of (1-Benzyl-pyrrolidin-3-ylmethyl)-methyl-amine

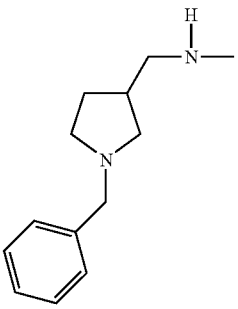

To a cooled (−5° C.) and stirred solution of LAH (1 M, 7.6 ml) in dry THF (75 ml) was added a solution of (1-benzyl-pyrrolidin-3-ylmethyl)-carbamic acid tert-butyl ester (1.47 g, 5.06 mmol) in THF (22 ml) over 20 minutes. The mixture was then heated at reflux for 2.5 hrs and cooled to room temperature and quenched by successive addition of ethyl acetate (50 ml). The organic layer was then washed with water (2×), 10% NaOH and brine, dried and evaporated to give the desired product in 90% yield.

B. Synthesis of (1-benzyl-pyrrolidin-3-ylmethyl)-carbamic acid tert-butyl ester methyl amine

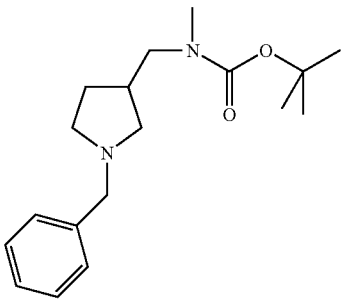

A solution of (1-benzyl-pyrrolidin-3-ylmethyl)-methyl amine (1.03 g, 5.04 mmol) in THF (30 ml), water (1 ml) and NaOH (0.5 ml) was cooled to 0° C. $(BOC)_2O$ (1.32 g, 6.05 mmol) was then added and reaction was stirred at room temperature for 2 hrs. The solvent was evaporated and the residue was partitioned between 2N aq. NaOH and $CH_2Cl_2$. The organic phase was washed with brine, dried and evaporated to dryness to give the desired product in 92% yield.

C. Synthesis of (Methyl-pyrrolidine-3-ylmethyl-amine)-carbamic acid tert-butyl ester

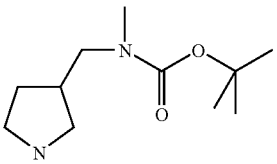

To a solution of (1-benzyl-pyrrolidin-3-ylmethyl)-carbamic acid tert-butyl ester methyl amine (1.0 g, 3.28 mmol) in methanol (35 ml) was added Pd/C (20%) (0.22 g). The resulting mixture was hydrogenated at 50 Psi over night. The Pd was filtered over Celite and evaporated to dryness to give the desired product in 92% yield.

D. Synthesis of (1-Benzhydryl-pyrrolidin-3-ylmethyl)-methyl-carbamic acid tert-butyl ester

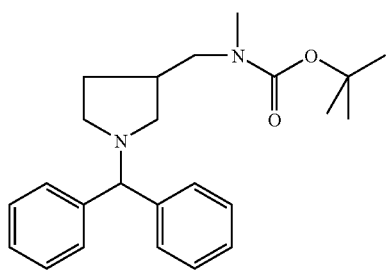

To a solution of chlorodiphenylmethane (0.79 g, 3.22 mmol) in butanone (20 ml) was added methyl-pyrrolidine-3-ylmethyl-amine)-carbamic acid tert-butyl ester (0.69 g, 3.22 mmol), $K_2CO_3$ (0.54 g, 3.8 mmol) and KI (0.54 g, 3.22 mmol). The mixture was heated under reflux for 18 hours, then filtered and the solvent was removed in vacuo. The residue was dissolved in $CH_2Cl_2$ (50 ml) and washed with water (10 ml). Drying over $MgSO_4$ and removal of solvent under reduced pressure followed by column chromatography using $CH_2Cl_2$:$CH_3OH$ (20:1) gives the desired product in 75% yield.

E. Synthesis of (1-Benzhydryl-pyrrolidin-3-ylmethyl)-methyl-amine

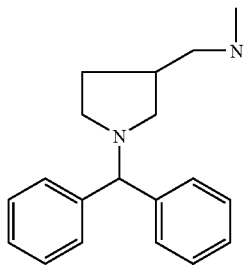

(1-Benzhydryl-pyrrolidin-3-ylmethyl)methyl carbamic acid-tert-butyl ester (0.47 g, 1.67 mmol) was dissolved in dry $CH_2Cl_2$ (15 ml) followed by addition of TFA (8 ml). The resulting solution was stirred at r.t. for 2 hrs. The solution was concentrated under reduced pressure. The resulting residue was dissolved in water (12 ml) and pH of the solution was adjusted to 10. The water phase was extracted with $CH_2Cl_2$ (100 ml), and dried over magnesium sulfate. The solvent was evaporated under reduced pressure to give the desired product in almost quantitative yield.

F. Synthesis of Final Product

To a solution of (1-benzhydryl pyrrolidin-3-ylmethyl-methyl amine (0.31 g, 1.10 mmol) in dry $CH_2Cl_2$ (25 ml) was added 3,3-diphenylpropionic acid (0.25 g, 1.10 mmol) under nitrogen. To the reaction was added EDC (0.42 g, 2.2 mmol) and DMAP (cat) and the reaction mixture stirred under nitrogen at room temp. overnight. The reaction was then concentrated under reduced pressure. The residue dissolved in ethyl acetate: water (10:1) (100 ml). The organic was washed with water (20 ml, 2×) and 10% NaOH (20 ml) and dried over $MgSO_4$ and evaporated to dryness. The resulting residue was purified by column chromatography using $CH_2Cl_2$:$CH_3OH$ (15:1) to give a desired product in good yield.

EXAMPLE 11

Assessment of Calcium Channel Blocking Activity

Antagonist activity was measured using whole cell patch recordings on human embryonic kidney cells either stably or transiently expressing rat $\alpha_{1B}+\alpha_2\delta+\beta_{1b}$ channels (N-type channels) with 5 mM barium as a charge carrier. P/Q-type channels ($\alpha_{1A}+\alpha_2\delta+\beta_{1b}$ cDNA subunits) and L-type channels ($\alpha_{1C}+\alpha_2\delta+\beta_{1b}$ cDNA subunits) were also transiently expressed in HEK 293 cells.

For transient expression, host cells, such as human embryonic kidney cells, HEK 293 (ATCC# CRL 1573) were grown in standard DMEM medium supplemented with 2 mM glutamine and 10% fetal bovine serum. HEK 293 cells were transfected by a standard calcium-phosphate-DNA coprecipitation method using the rat $\alpha_{1B}+\beta_{1b}+\alpha_2\delta$ N-type calcium channel subunits in a vertebrate expression vector (for example, see Current Protocols in Molecular Biology).

After an incubation period of from 24 to 72 hrs the culture medium was removed and replaced with external recording solution (see below). Whole cell patch clamp experiments were performed using an Axopatch 200B amplifier (Axon Instruments, Burlingame, Calif.) linked to an IBM compatible personal computer equipped with pCLAMP software. Borosilicate glass patch pipettes (Sutter Instrument Co., Novato, Calif.) were polished (Microforge, Narishige, Japan) to a resistance of about 4 MΩ when filled with cesium methanesulfonate internal solution (composition in MM: 109 $CsCH_3$ $SO_4$, 4 $MgCl_2$, 9 EGTA, 9 HEPES, pH 7.2). Cells were bathed in 5 mM $Ba^{++}$ (in mM: 5 $BaCl_2$, 1 $MgCl_2$, 10 HEPES, 40 tetraethylammonium chloride, 10 glucose, 87.5 CsCl pH 7.2). Current data shown were elicited by a train of 100 ms test pulses at 0.066 Hz from −100 mV and/or −80 mV to various potentials (min. −20 mV, max. +30 mV). Drugs were perfused directly into the vicinity of the cells using a microperfusion system.

Normalized dose-response curves were fit (Sigmaplot 4.0, SPSS Inc., Chicago, Ill.) by the Hill equation to determine $IC_{50}$ values. Steady-state inactivation curves were plotted as the normalized test pulse amplitude following 5 s inactivating prepulses at +10 mV increments. Inactivation curves were fit (Sigmaplot 4.0) with the Boltzman equation, $I_{peak}$ (normalized)=$1/(1+\exp((V-V_h)z/25.6))$, where V and $V_h$ are the conditioning and half inactivation potentials, respectively, and z is the slope factor.

FIG. 1 is a graph that shows the selectivity of compound P13 for N-type calcium channels over L-type and P/Q-type channels. P13 is approximately 21-fold more selective for N-type over P/Q-type channels and greater than 100-fold selective for N-type over L-type channels.

FIG. 2 is a graph that shows the selectivity of compound P17 for N-type calcium channels over L-type and P/Q-type channels. P17 is approximately 31-fold more selective for N-type over P/Q-type channels and greater than 75-fold selective for N-type over L-type channels.

EXAMPLE 12

N-type Channel Blocking Activities of Various Invention Compounds

The methods of Examples 1 and 2 were followed with slight modifications as will be apparent from the description below.

A. Transformation of HEK Cells:

N-type calcium channel blocking activity was assayed in human embryonic kidney cells, HEK 293, stably transfected with the rat brain N-type calcium channel subunits ($\alpha_{1B}$+$\alpha_2\delta$+$\beta_{1b}$ cDNA subunits). Alternatively, N-type calcium channels ($\alpha_{1B}$+$\alpha_2\delta$+$\beta_{1b}$ cDNA subunits), L-type channels ($\alpha_{1C}$+$\alpha_2\delta$+$\beta_{1b}$ cDNA subunits) and P/Q-type channels ($\alpha_{1A}$+$\alpha_2\delta$+$\beta_{1b}$ cDNA subunits) were transiently expressed in HEK 293 cells. Briefly, cells were cultured in Dulbecco's modified eagle medium (DMEM) supplemented with 10% fetal bovine serum, 200 U/ml penicillin and 0.2 mg/ml streptomycin at 37° C. with 5% $CO_2$. At 85% confluency cells were split with 0.25% trypsin/1 mM EDTA and plated at 10% confluency on glass coverslips. At 12 hours the medium was replaced and the cells transiently transfected using a standard calcium phosphate protocol and the appropriate calcium channel cDNA's. Fresh DMEM was supplied and the cells transferred to 28° C./5% $CO_2$. Cells were incubated for 1 to 2 days to whole cell recording.

B. Measurement of Inhibition

Whole cell patch clamp experiments were performed using an Axopatch 200B amplifier (Axon Instruments, Burlingame, Calif.) linked to a personal computer equipped with pCLAMP software. The external and internal recording solutions contained, respectively, 5 mM $BaCl_2$, 10 mM $MgCl_2$, 10 mM HEPES, 40 mM TEACl, 10 mM glucose, 87.5 mM CsCl (pH 7.2) and 108 mM CsMS, 4 mM $MgCl_2$, 9 mM EGTA, 9 mM HEPES (pH 7.2). Currents were typically elicited from a holding potential of −80 mV to +10 mV using Clampex software (Axon Instruments). Typically, currents were first elicited with low frequency stimulation (0.067 Hz) and allowed to stabilize prior to application of the compounds. The compounds were then applied during the low frequency pulse trains for two to three minutes to assess tonic block, and subsequently the pulse frequency was increased to 0.2 Hz to assess frequency dependent block. Data were analyzed using Clampfit (Axon Instruments) and SigmaPlot 4.0 (Jandel Scientific).

Specific data obtained for N-type channels are shown in Table 3 below.

TABLE 3

N-type Calcium Channel Block

| Compound | $IC_{50}$ at 0.067 Hz (nM) | $IC_{50}$ at 0.2 Hz (nM) |
| --- | --- | --- |
| P1 | 61 | Not tested |
| P2 | 1070 | 840 |
| P3 | 417 | Not tested |
| P4 | 400 | Not tested |
| P5 | 59 | Not tested |
| P6 | 212 | Not tested |
| P7 | 49 | Not tested |
| P8 | 35 | Not tested |
| P9 | 15 | Not tested |
| P11 | 10 | Not tested |
| P12 | 32 | Not tested |
| P13 | 41 | Not tested |
| P14 | 39 | Not tested |
| P15 | >1000 | Not tested |
| P17 | 60 | Not tested |
| P18 | 28 | Not tested |
| P19 | 250 | 94 |
| P20 | 450 | 280 |
| P21 | 210 | 150 |
| P23 | 410 | 200 |
| P24 | 380 | 210 |
| P25 | 110 | 78 |
| P26 | 263 | 236 |
| P31 | 563 | 220 |
| P36 | 100 | 20 |
| P37 | 23 | 8 |
| P38 | 80 | 24 |
| P39 | 179 | 257 |
| P40 | 19 | 3 |
| P41 | 485 | 149 |
| P42 | 618 | 356 |
| P43 | 266 | 159 |
| P44 | 265 | 119 |
| P45 | 512 | 247 |
| P46 | 7 | 1 |
| P47 | 295 | 185 |
| P48 | 133 | 99 |
| P49 | 136 | 89 |
| P50 | 76 | 53 |
| P51 | 72 | 56 |
| P52 | 135 | 110 |
| P53 | 223 | 157 |
| P54 | 279 | 241 |
| P55 | 326 | 226 |
| P56 | 137 | 92 |
| P57 | 225 | 81 |
| P58 | 120 | 86 |
| P59 | 8000 | 2000 |
| P60 | 57 | 45 |
| P63 | 380 | 330 |

EXAMPLE 13

T-type Channel Blocking Activities of Various Invention Compounds

Standard patch-clamp techniques were employed to identify blockers of T-type currents. Briefly, previously described HEK cell lines stably expressing human $\alpha_{1G}$ T-type channels were used for all the recordings (passage #: 4-20, 37° C., 5% $CO_2$). To obtain T-type currents, plastic dishes containing semi-confluent cells were positioned on the stage of a ZEISS AXIOVERT S100 microscope after replacing the culture medium with external solution (see below). Whole-cell patches were obtained using pipettes (borosilicate glass with filament, O.D.: 1.5 mm, I.D.: 0.86 mm, 10 cm length), fabricated on a SUTTER P-97 puller with resistance values of ~5 MΩ (see below for internal solution).

TABLE 4

External Solution 500 ml - pH 7.4, 265.5 mOsm

| Salt | Final mM | Stock M | Final ml |
|---|---|---|---|
| CsCl | 132 | 1 | 66 |
| $CaCl_2$ | 2 | 1 | 1 |
| $MgCl_2$ | 1 | 1 | 0.5 |
| HEPES | 10 | 0.5 | 10 |
| glucose | 10 | — | 0.9 grams |

TABLE 5

Internal Solution 50 ml - pH 7.3 with CsOH, 270 mOsm

| Salt | Final mM | Stock M | Final ml |
|---|---|---|---|
| Cs-Methanesulfonate | 108 | — | 1.231 gr/50 ml |
| MgCl2 | 2 | 1 | 0.1 |
| HEPES | 10 | 0.5 | 1 |
| EGTA-Cs | 11 | 0.25 | 2.2 |
| ATP | 2 | 0.2 | 0.025 (1 aliquot/2.5 ml) |

T-type currents were reliably obtained by using two voltage protocols:
(1) "non-inactivating", and
(2) "inactivation"

In the non-inactivating protocol, the holding potential is set at −110 mV and with a pre-pulse at −100 mV for 1 second prior to the test pulse at −40 mV for 50 ms. In the inactivation protocol, the pre-pulse is at approximately −85 mV for 1 second, which inactivates about 15% of the T-type channels.

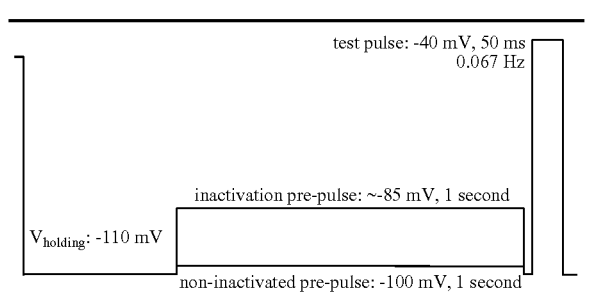

Test compounds were dissolved in external solution, 0.1-0.01% DMSO. After ~10 min rest, they were applied by gravity close to the cell using a WPI microfil tubing. The "non-inactivated" pre-pulse was used to examine the resting block of a compound. The "inactivated" protocol was employed to study voltage-dependent block. However, the initial data shown below were mainly obtained using the non-inactivated protocol only. $IC_{50}$ values are shown for various compounds of the invention in Table 6.

TABLE 6

Block of $α_{1G}$ T-type Channels

| Compound | $IC_{50}$ at −100 mV (nM) | $IC_{50}$ at −80 mV (nM) |
|---|---|---|
| P2 | 326 | 52 |
| P3 | 86 | Not tested |
| P5 | No effect | Not tested |
| P11 | 27 | Not tested |
| P13 | 1.5 | 0.7 |
| P15 | >10,000 | Not tested |

TABLE 6-continued

Block of $α_{1G}$ T-type Channels

| Compound | $IC_{50}$ at −100 mV (nM) | $IC_{50}$ at −80 mV (nM) |
|---|---|---|
| P17 | 29 | Not tested |
| P19 | 70 | Not tested |
| P24 | 12 | Not tested |
| P26 | 137 | 42 |
| P31 | 460 | 196 |
| P36 | 30 | 12 |
| P37 | 111 | 28 |
| P38 | 94 | 21 |
| P39 | 12 | 3 |
| P40 | 328 | 105 |
| P41 | 21 | 6 |
| P42 | 94 | 59 |
| P43 | 48 | 15 |
| P44 | 52 | 29 |
| P45 | 410 | 67 |
| P46 | 23 | 5 |
| P47 | 24 | 8 |
| P48 | 4.8 | 1.9 |
| P49 | 18 | 8 |
| P54 | 153 | 55 |
| P55 | 57 | 18 |
| P57 | 115 | 28 |
| P58 | 79 | 58 |
| P59 | 40000 | 6000 |
| P60 | 618 | 227 |

EXAMPLE 14

Activity of Invention Compounds in Formalin-Induced Pain Model

The effects of intrathecally delivered compounds of the invention on the rat formalin model were measured. The compounds were reconstituted to stock solutions of approximately 10 mg/ml in propylene glycol. Eight Holtzman male rats of 275-375 g size were randomly selected per test article.

The following study groups were used, with test article, vehicle control (propylene glycol) and saline delivered intraperitoneally (IP):

TABLE 7

Formalin Model Dose Groups

| Test/Control Article | Dose | Route | Rats per group |
|---|---|---|---|
| Compound | 30 mg/kg | IP | 6 |
| Propylene glycol | N/A | IP | 4 |
| Saline | N/A | IP | 7 |

N/A = Not Applicable

Prior to initiation of drug delivery baseline behavioral and testing data were taken. At selected times after infusion of the Test or Control Article these data were again collected.

On the morning of testing, a small metal band (0.5 g) was loosely placed around the right hind paw. The rat was placed in a cylindrical Plexiglas chamber for adaptation a minimum of 30 minutes. Test Article or Vehicle Control Article was administered 10 minutes prior to formalin injection (50 μl of 5% formalin) into the dorsal surface of the right hindpaw of the rat. The animal was then placed into the chamber of the automated formalin apparatus where movement of the formalin injected paw was monitored and the number of paw flinches tallied by minute over the next 60 minutes (Malmberg, A. B., et al., *Anesthesiology* (1993) 79:270-281).

Results are presented as Maximum Possible Effect±SEM, where saline control=100%.

TABLE 8

Efficacy of Invention Compounds in Formalin-Induced Pain Model

| Compound | Phase I | Phase II | Phase IIA |
|---|---|---|---|
| P13 | 85 ± 9 | 86 ± 7 | 86 ± 5 |
| P17 | 74 ± 8 | 84 ± 9 | 79 ± 9 |
| P24 | 66 ± 11 | 38 ± 7 | 20 ± 4 |

The invention claimed is:

1. A compound of the formula

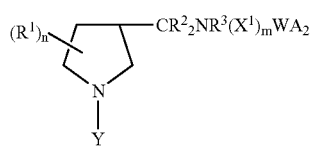
(1)

or

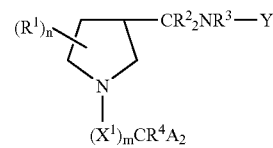
(2)

or the salts thereof, including all stereoisomeric forms thereof wherein:

Y is $(X^2)_l A$ or $(X^1)_m CR^4 A_2$;
W is $CR^4$ or N;
n is 0-3;
l and m are independently 0 or 1;
each $X^1$ and $X^2$ is independently optionally substituted alkylene (1-10C) or alkenylene (2-10C) wherein one or more said C may optionally be replaced by N or O;
each A is independently a 5-7 membered optionally substituted carbocyclic aromatic or aliphatic ring;
wherein each $R^1$ is independently optionally substituted lower alkyl (1-6C), optionally substituted lower alkenyl (2-6C), or optionally substituted lower alkynyl (2-6C), each optionally including one or more heteroatoms selected from O, N and S or is an inorganic substituent;
wherein each $R^2$ is independently H, lower alkyl, lower alkenyl or halo;
wherein $R^3$ is H, lower alkyl, lower alkenyl, or lower acyl, wherein one or more carbons of each of the foregoing is replaced with a heteroatom; and
wherein $R^4$ is H, alkyl, alkenyl, arylalkyl, arylalkenyl, hydroxy, alkoxy, sulfhydryl, alkylsulfhydryl, amino or alkylamino.

2. The compound of claim 1, wherein each $R^1$ and each said optional substituent is independently halo, $NO_2$, $SO_2$, SO, NO, =O, =NOH and n is 0-3.

3. The compound of claim 1, wherein each $R^2$ is independently H or lower alkyl.

4. The compound of claim 3, wherein at least one $R^2$ is H.

5. The compound of claim 1, wherein $R^3$ is H or $CONCH_2CH_3$.

6. The compound of claim 1, wherein $R^4$ is H, hydroxy or alkoxy.

7. The compound of claim 6, wherein $R^4$ is H.

8. The compound of claim 1, wherein $X^1$ is alkylene or alkenylene unsubstituted or substituted by =O.

9. The compound of claim 8, wherein said =O is at the carbon adjacent the nitrogen to which $X^1$ is coupled.

10. The compound of claim 1, wherein $X^2$ is alkylene or alkenylene unsubstituted or substituted by =O.

11. The compound of claim 10, wherein said =O is at the carbon adjacent the nitrogen to which $X^2$ is coupled.

12. The compound of claim 1, wherein each A is independently optionally substituted phenyl, or optionally substituted cyclohexyl.

13. The compound of claim 12, wherein substituted phenyl or substituted cyclohexyl is substituted by substituents selected from the group consisting of inorganic substituents, alkyl, alkenyl, alkynyl, aryl, alkylaryl, and alkenylaryl, in each case optionally substituted, wherein said alkyl, alkenyl or alkynyl may optionally contain one or more heteroatoms in place of carbon.

14. The compound of claim 13, wherein each of said substituents is independently halo, alkoxy or alkyl.

15. A compound of claim 1 which is of the formula

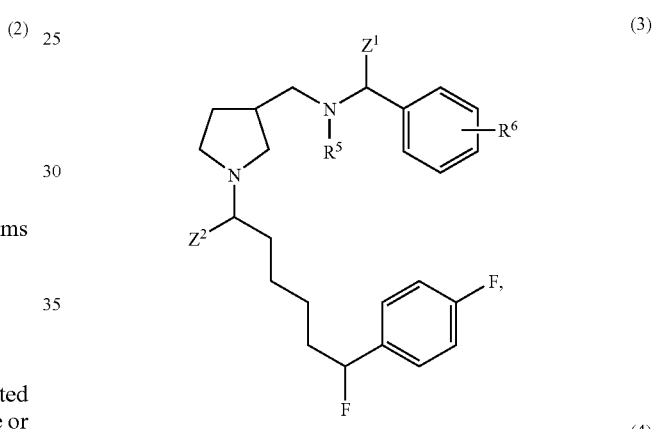
(3)

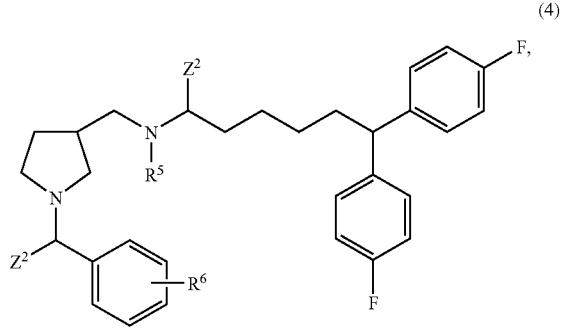
(4)

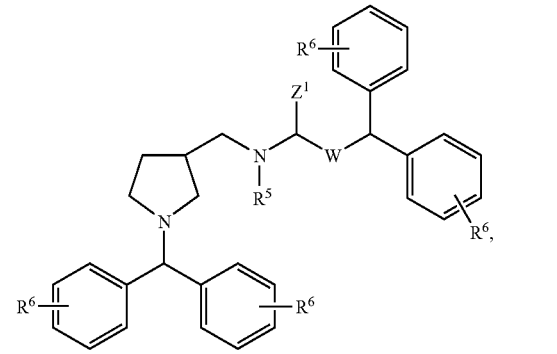
(5)

-continued

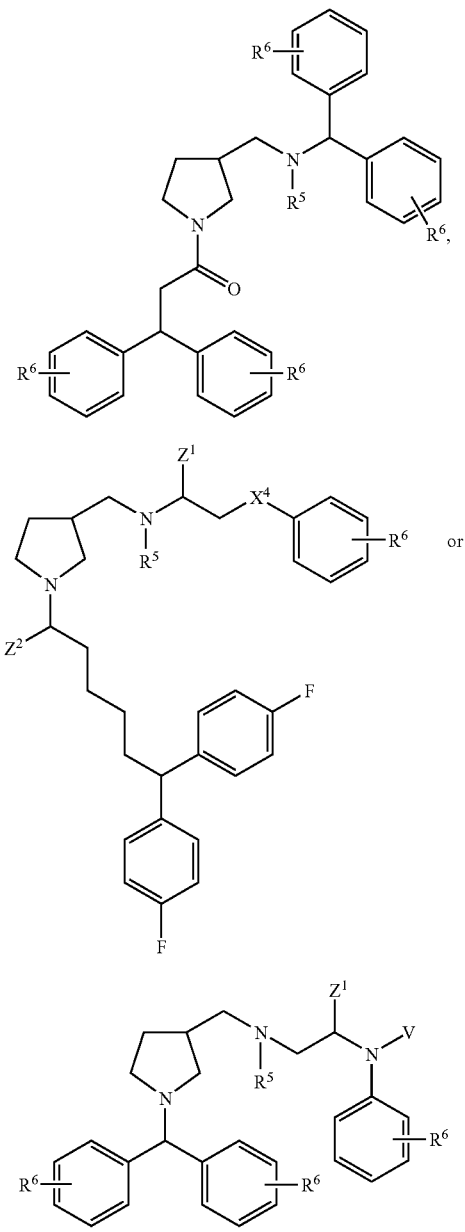

wherein:
each $Z^1$ and $Z^2$ is independently $H_2$ or =O;
$R^5$=H, optionally substituted alkyl, $(CR_2)_nCONR^7{}_2$, $(CR_2)^nNR^7{}_2$ where each $R^7$ is H, lower alkyl or aryl; n=0-1;
V is alkyl or phenyl, each optionally substituted;
W is $CR_2$ or NR;
$X^4$ is O, S, N or NCO; and
$R^6$ represents 0-3 substituents wherein said substituents are independently alkyl (1 -6C), optionally containing 1-4 heteroatoms (halo, N, O, or S), or aryl (6-10C) or arylalkyl (7-16C) and/or said substituents are halo, $CF_3$, OCF, $NO_2$, $NR_2$, OR, SR, COR, COOR, $CONR_2$, NROCR, or OOCR;
and wherein each R=H or alkyl (1-8C).

16. The compound of claim 1 which is
N-(1-benzhydryl-pyrrolidin-3-ylmethyl)-3,3-diphenyl-propionamide;
1-{3-[(benzhydryl-amino)-methyl]-pyrrolidin-1-yl}-3,3-diphenyl-propan-1-one;
N-{1-[6,6-Bis-(4-fluoro-phenyl)-hexanoyl]-pyrrolidin-3-ylmethyl}-3,4,5-trimethoxy-benzamide;
{1-[6,6-bis-(4-fluoro-phenyl)-hexyl]-pyrrolidin-3-ylmethyl}-(3,4,5-trimethoxy-benzyl)-amine;
6,6-bis-(4-fluoro-phenyl)-hexanoic acid [1-(3,4,5-trimethoxy-benzoyl)-pyrrolidin-3-ylmethyl]-amide;
[6,6-bis-(4-fluoro-phenyl)-hexyl]-[1-(3,4,5-trimethoxy-benzyl)-pyrrolidin-3-ylmethyl]-amine;
N-{1-[6,6-bis-(4-fluoro-phenyl)-hexanoyl]-pyrrolidin-3-ylmethyl}-3,5-di-tert-butyl-4-hydroxy-benzmide;
4-[({1-[6,6-bis-(4-fluoro-phenyl)-hexyl]-pyrrolidin-3-ylmethyl}-amino)-methyl]-2,6-di-tert-butyl-phenol;
6,6-bis-(4-fluoro-phenyl)-hexanoic acid [1-(3,5-di-tert-butyl-4-hydroxy-benzoyl)-pyrrolidin-3-ylmethyl]-amide;
4-(3-{[6,6-bis-(4-fluoro-phenyl)-hexylamino]-methyl}-pyrrolidin-1-ylmethyl)-2,6-di-tert-butyl-phenol;
6,6-bis-(4-fluoro-phenyl)-hexanoic acid [1-(3,5-di-tert-butyl-4-methoxy-benzoyl)-pyrrolidin-3-ylmethyl]-amide;
[6,6-bis-(4-fluoro-phenyl)-hexyl]-[1-(3,5-di-tert-butyl-4-methoxy-benzyl)-pyrrolidin-3-ylmethyl]-amine;
N-{1-[6,6-bis-(4-fluoro-phenyl)-hexanoyl]-pyrrolidin-3-ylmethyl}-3,5-di-tert-butyl-4-methoxy-benzamide;
{1-[6,6-bis-(4-fluoro-phenyl)-hexyl]-pyrrolidin-3-ylmethyl}-(3,5-di-tert-butyl-4-methoxy-benzyl)-amine;
N-{1-[6,6-bis-(4-fluoro-phenyl)-hexanoyl]-pyrrolidin-3-ylmethyl}-3,5-dibromo-4-hydroxy-benzamide;
4-[({1-[6,6-bis-(4-fluoro-phenyl)-hexyl]-pyrrolidin-3-ylmethyl}-amino)-methyl]-2,6-dibromo-phenol;
N-{1-[6,6-bis-(4-fluoro-phenyl)-hexanoyl]-pyrrolidin-3-ylmethyl}-3,5-di-tert-butyl-benzamide;
{1-[6,6-bis-(4-fluoro-phenyl)-hexyl]-pyrrolidin-3-ylmethyl}-(3,5-di-tert-butyl-benzyl)-amine;
N-{1-[6,6-bis-(4-fluoro-phenyl)-hexyl]-pyrrolidin-3-ylmethyl}-3,5-di-tert-butyl-4-methoxy-benzamide;
N-{1-[6,6-bis-(4-fluoro-phenyl)-hexyl]-pyrrolidin-3-ylmethyl}-3,4,5-trimethoxy-benzamide;
N-{1-[6,6-bis-(4-fluoro-phenyl)-hexyl]-pyrrolidin-3-ylmethyl}-3,5-bis-trifluoromethyl-benzamide;
N-{1-[6,6-bis-(4-fluoro-phenyl)-hexanoyl]-pyrrolidin-3-ylmethyl}-3,5-di-tert-butyl-4-(2-dimethylamino-ethoxy)-benzamide;
6,6-bis-(4-fluoro-phenyl)-hexanoic acid {1-[3,5-di-tert-butyl-4-(2-dimethylamino-ethoxy)-benzoyl]-pyrrolidin-3-ylmethyl}-amide;
N-{1-[6,6-bis-(4-fluoro-phenyl)-hexanoyl]-pyrrolidin-3-ylmethyl}-3,5-bis-trifluoromethyl-benzamide;
N-{1-[6,6-bis-(4-fluoro-phenyl)-hexanoyl]-pyrrolidin-3-ylmethyl}-4-tert-butyl-benzamide;
N-{1-[(4-chloro-phenyl)-phenyl-methyl]-pyrrolidin-3-ylmethyl}-3,3-diphenyl-propionamide;
N-{1-[6,6-bis-(4-fluoro-phenyl)-hexanoyl]-pyrrolidin-3-ylmethyl}-2-phenoxy-acetamide;
N-{1-[6,6-bis-(4-fluoro-phenyl)-hexanoyl]-pyrrolidin-3-ylmethyl}-2-phenylsulfanyl-acetamide;
N-{1-[6,6-bis-(4-fluoro-phenyl)-hexanoyl]-pyrrolidin-3-ylmethyl}-2-phenylamino-acetamide;
N-[2-({1-[6,6-bis-(4-fluoro-phenyl)-hexanoyl]-pyrrolidin-3-ylmethyl}-amino)-ethyl]-3,4,5-trimethoxy-benzamide;

N-{1-[6,6-bis-(4-fluoro-phenyl)-hexanoyl]-pyrrolidin-3-ylmethyl}-2-(2,4-difluoro-phenoxy)-acetamide;
1-(1-benzhydryl-pyrrolidin-3-ylmethyl)-1-(3,3-diphenyl-propionyl)-3-ethyl-urea;
1-{1-[6,6-bis-(4-fluoro-phenyl)-hexanoyl]-pyrrolidin-3-ylmethyl}-3-ethyl-1-(2-phenylsulfanyl-acetyl)-urea;
1-{1-[6,6-bis-(4-fluoro-phenyl)-hexanoyl]-pyrrolidin-3-ylmethyl}-3-ethyl-1-(2-phenylamino-acetyl)-urea;
1-{1-[6,6-bis-(4-fluoro-phenyl)-hexanoyl]-pyrrolidin-3-ylmethyl}-1-[2-(2,4-difluoro-phenoxy)-acetyl]-3-ethyl-urea;
N-{1-[6,6-bis-(4-fluoro-phenyl)-hexanoyl]-pyrrolidin-3-ylmethyl}-2-(4-chloro-phenoxy)-acetamide;
N-{1-[(2-chloro-phenyl)-phenyl-methyl]-pyrrolidin-3-ylmethyl}-3,3-diphenyl-propionamide;
N-{1-[(3-chloro-phenyl)-phenyl-methyl]-pyrrolidin-3-ylmethyl}-3,3-diphenyl-propionamide;
3,3-diphenyl-N-{1-[phenyl-(4-trifluoromethyl-phenyl)-methyl]-pyrrolidin-3-ylmethyl}-propionamide;
N-{1-[6,6-bis-(4-fluoro-phenyl)-hexanoyl]-pyrrolidin-3-ylmethyl}-2-(3,5-dimethyl-phenylamino)-acetamide;
N-{1-[6,6-bis-(4-fluoro-phenyl)-hexanoyl]-pyrrolidin-3-ylmethyl}-2-(3,5-dimethyl-phenylamino)-acetamide;
R-N-{1-[6,6-bis-(4-fluoro-phenyl)-hexanoyl]-pyrrolidin-3-ylmethyl}-3,5-di-tert-butyl-4-methoxy-benzamide;
S-N-{1-[6,6-bis-(4-fluoro-phenyl)-hexanoyl]-pyrrolidin-3-ylmethyl}-3,5-di-tert-butyl-4-methoxy-benzamide;
R-N-{1-[6,6-bis-(4-fluoro-phenyl)-hexanoyl]-pyrrolidin-3-ylmethyl}-3,5-di-tert-butyl-benzamide;
S-N-{1-[6,6-bis-(4-fluoro-phenyl)-hexanoyl]-pyrrolidin-3-ylmethyl}-3,5-di-tert-butyl-benzamide;
N-(1-benzhydryl-pyrrolidin-3-ylmethyl)-2-diphenylamino-acetamide;
2-{(1-benzhydryl-pyrrolidin-3-ylmethyl)-[(diphenylcarbamoyl)-methyl]-amino}-N,N-diphenyl-acetamide;
1-benzhydryl-3-(1-benzhydryl-pyrrolidin-3-ylmethyl)-urea;
S-N-{1-[6,6-bis-(4-fluoro-phenyl)-hexanoyl]-pyrrolidin-3-ylmethyl}-3,5-bis-trifluoromethyl-benzamide;
R-N-{1-[6,6-bis-(4-fluoro-phenyl)-hexanoyl]-pyrrolidin-3-ylmethyl}-3,5-bis-trifluoromethyl-benzamide;
3,3-bis-(4-fluoro-phenyl)-N-{1-[(4-fluoro-phenyl)-phenyl-methyl]-pyrrolidin-3-ylmethyl}-propionamide;
N-(1-benzhydryl-pyrrolidin-3-ylmethyl)-3,3-bis-(4-fluoro-phenyl)-propionamide;
N-{1-[(4-tert-butyl-phenyl)-phenyl-methyl]-pyrrolidin-3-ylmethyl}-3,3-bis-(4-fluoro-phenyl)-propionamide;
N-(1-benzhydryl-pyrrolidin-3-ylmethyl)-N-methyl-3,3-diphenyl-propionamide;
2-[(1-benzhydryl-pyrrolidin-3-ylmethyl)-methyl-amino]-N,N-diphenyl-acetamide;
N-(1-benzhydryl-pyrrolidin-3-ylmethyl)-N-methyl-N',N'-diphenyl-ethane-1,2-diamine;
(1-benzhydryl-pyrrolidin-3-ylmethyl)-(3,3-diphenyl-propyl)-methyl-amine;
1-(3-{[(3,5-bis-trifluoromethyl-benzyl)-methyl-amino]-methyl}-pyrrolidin-1-yl)-6,6-bis-(4-fluoro-phenyl)-hexan-1-one;
6,6-bis-(4-fluoro-phenyl)-1-(3-{[methyl-(3,4,5-trimethoxy-benzyl)-amino]-methyl}-pyrrolidin-1-yl)-hexan-1-one;
N-(1-benzhydryl-pyrrolidin-3-ylmethyl)-N-(2-diphenylamino-ethyl)-N',N'-diphenyl-ethane-1,2-diamine;
N-{1-[6,6-bis-(4-fluoro-phenyl)-hexanoyl]-pyrrolidin-3-ylmethyl}-3-fluoro-5-trifluoromethyl-benzamide;
N-{1-[6,6-bis-(4-fluoro-phenyl)-hexanoyl]-pyrrolidin-3-ylmethyl}-4-fluoro-3-trifluoromethyl-benzamide; or
[3-({[6,6-bis-(4-fluoro-phenyl)-hexyl]-methyl-amino}-methyl)-pyrrolidin-1-yl]-(3,4,5-trimethoxy-phenyl)-methanone.

17. A pharmaceutical composition for use in treating stroke or pain which composition comprises, in admixture with a pharmaceutically acceptable excipient, a dosage amount of the compound of claim 1.

18. A method to treat stroke or pain in a subject which method comprises administering to a subject in need of such treatment an effective amount of the compound of claim 1 or a pharmaceutical composition thereof.

* * * * *